United States Patent
Berkenblit et al.

(10) Patent No.: US 9,211,291 B2
(45) Date of Patent: Dec. 15, 2015

(54) TREATMENT REGIMEN UTILIZING NERATINIB FOR BREAST CANCER

(75) Inventors: Anna Berkenblit, Needham, MA (US); Florence Marie Helene Binlich, Ville d'Avray (FR); Paul Goss, Wellesley, MA (US)

(73) Assignee: WYETH LLC, New York, NY (US)

( * ) Notice: Subject to any disclaimer, the term of this patent is extended or adjusted under 35 U.S.C. 154(b) by 0 days.

(21) Appl. No.: 13/256,910

(22) PCT Filed: Mar. 24, 2010

(86) PCT No.: PCT/US2010/028448
§ 371 (c)(1),
(2), (4) Date: Nov. 23, 2011

(87) PCT Pub. No.: WO2010/117633
PCT Pub. Date: Oct. 14, 2010

(65) Prior Publication Data
US 2012/0071507 A1    Mar. 22, 2012

Related U.S. Application Data

(60) Provisional application No. 61/166,796, filed on Apr. 6, 2009.

(51) Int. Cl.
| A61K 31/47 | (2006.01) |
| A61K 31/435 | (2006.01) |
| A61K 31/4706 | (2006.01) |
| A61K 39/395 | (2006.01) |
| A61K 45/06 | (2006.01) |

(52) U.S. Cl.
CPC ....... *A61K 31/4706* (2013.01); *A61K 39/39558* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 4,966,891 A | 10/1990 | Fujiu et al. |
| 5,453,497 A | 9/1995 | Kamiya et al. |
| 5,472,949 A | 12/1995 | Arasaki et al. |
| 5,476,932 A | 12/1995 | Brinkman et al. |
| 5,760,041 A | 6/1998 | Wissner et al. |
| 6,002,008 A | 12/1999 | Wissner et al. |
| 6,143,764 A | 11/2000 | Kubo et al. |
| 6,251,912 B1 | 6/2001 | Wissner et al. |
| 6,288,082 B1 | 9/2001 | Wissner et al. |
| 6,297,258 B1 | 10/2001 | Wissner et al. |
| 6,384,051 B1 | 5/2002 | Frost et al. |
| 6,387,371 B1 | 5/2002 | Hudziak et al. |
| 6,399,063 B1 | 6/2002 | Hudziak et al. |
| 6,432,979 B1 | 8/2002 | Frost et al. |
| 6,511,986 B2 | 1/2003 | Zhang et al. |
| 6,617,333 B2 | 9/2003 | Rabindran et al. |
| 6,780,996 B2 | 8/2004 | Boschelli et al. |
| 6,821,515 B1 | 11/2004 | Cleland et al. |
| 6,821,988 B2 | 11/2004 | Wissner et al. |
| 7,126,025 B2 | 10/2006 | Considine et al. |
| 7,189,735 B2 | 3/2007 | Dukart et al. |
| 7,294,468 B2 | 11/2007 | Bell et al. |
| 7,297,795 B2 | 11/2007 | Sutherland et al. |
| 7,306,801 B2 | 12/2007 | Caligiuri et al. |
| RE40,418 E | 7/2008 | Rabindran et al. |
| 7,399,865 B2 | 7/2008 | Wissner et al. |
| 7,846,936 B2 | 12/2010 | Hilberg et al. |
| 7,897,159 B2 | 3/2011 | Weber |
| 7,915,402 B2 | 3/2011 | Anderson et al. |
| 7,982,043 B2 | 7/2011 | Wissner et al. |
| 8,022,216 B2 | 9/2011 | Lu et al. |
| 8,173,814 B2 | 5/2012 | Lu et al. |
| 8,338,456 B2 | 12/2012 | Coughlin et al. |
| 8,394,959 B2 | 3/2013 | Lu et al. |
| 8,518,446 B2 | 8/2013 | Ashraf et al. |
| 8,524,281 B2 | 9/2013 | Venkata Ramana Rao et al. |
| 8,669,273 B2 | 3/2014 | Zacharchuk et al. |
| 8,790,708 B2 | 7/2014 | Ashraf et al. |
| 2002/0183239 A1 | 12/2002 | Gibbons, Jr. et al. |
| 2002/0183240 A1 | 12/2002 | Gibbons et al. |
| 2002/0198137 A1 | 12/2002 | Dukart et al. |
| 2003/0149056 A1 | 8/2003 | Wissner et al. |
| 2003/0153593 A1 | 8/2003 | Dukart et al. |
| 2004/0162442 A1 | 8/2004 | Considine et al. |
| 2004/0176339 A1 | 9/2004 | Sherman et al. |
| 2004/0209930 A1 | 10/2004 | Carboni et al. |
| 2004/0258662 A1 | 12/2004 | Gibbons et al. |

(Continued)

FOREIGN PATENT DOCUMENTS

| | | |
|---|---|---|
| EP | 0693285 A2 | 1/1996 |
| EP | 1448531 B1 | 8/2007 |
| EP | 1663978 B1 | 11/2007 |
| EP | 1848414 B1 | 4/2011 |
| JP | 2003-519698 A | 6/2003 |
| WO | WO 92/22653 A1 | 12/1992 |
| WO | 9633978 A1 | 10/1996 |
| WO | 9633980 A1 | 10/1996 |
| WO | WO 98/43960 A1 | 10/1998 |
| WO | WO 00/018761 A1 | 4/2000 |

(Continued)

OTHER PUBLICATIONS

Reid et al. (European J. of Cancer 2007, 43:481-489).*

(Continued)

*Primary Examiner* — Jeffrey S. Lundgren
*Assistant Examiner* — Michael Schmitt
(74) *Attorney, Agent, or Firm* — Jones Day

(57) ABSTRACT

An extended regimen for treatment of HER-2/neu overexpressed/amplified cancer is described, with involves delivering a course of neratinib therapy to HER-2/neu overexpressed/amplified cancer patients following the completion of surgical and adjuvant therapy. The neratinib regimen may be continued for upwards of twelve months to five years. Also provided are pharmaceutical kits designed to facilitate compliance with the regimen.

18 Claims, No Drawings

(56) References Cited

U.S. PATENT DOCUMENTS

| | | |
|---|---|---|
| 2005/0025825 A1 | 2/2005 | Heasley et al. |
| 2005/0043233 A1 | 2/2005 | Stefanic et al. |
| 2005/0059678 A1 | 3/2005 | Wissner et al. |
| 2005/0129761 A1 | 6/2005 | Venkata Ramana Rao et al. |
| 2005/0136063 A1 | 6/2005 | Wang et al. |
| 2005/0187184 A1 | 8/2005 | Gibbons, Jr. et al. |
| 2005/0272758 A1 | 12/2005 | Bayever et al. |
| 2006/0030547 A1 | 2/2006 | Dukart et al. |
| 2006/0035904 A1 | 2/2006 | Gibbons et al. |
| 2006/0058311 A1 | 3/2006 | Munzert et al. |
| 2006/0079515 A1 | 4/2006 | Frost |
| 2006/0128793 A1 | 6/2006 | Zask et al. |
| 2006/0178387 A1 | 8/2006 | Fujimoto-Ouchi et al. |
| 2006/0235046 A1 | 10/2006 | Zacharchuk et al. |
| 2006/0270668 A1 | 11/2006 | Chew et al. |
| 2006/0270669 A1 | 11/2006 | Chew et al. |
| 2007/0014859 A1 | 1/2007 | Shah et al. |
| 2007/0104721 A1 | 5/2007 | Moore et al. |
| 2007/0105887 A1 | 5/2007 | Moore |
| 2007/0281932 A1 | 12/2007 | Bernier et al. |
| 2008/0112888 A1 | 5/2008 | Wang |
| 2008/0207615 A1 | 8/2008 | Bell et al. |
| 2008/0234264 A1 | 9/2008 | Bell et al. |
| 2008/0254040 A1 | 10/2008 | Stefanic et al. |
| 2008/0286771 A1 | 11/2008 | Hudson et al. |
| 2008/0286785 A1 | 11/2008 | Nishio et al. |
| 2009/0035269 A1 | 2/2009 | Weber |
| 2009/0047278 A1 | 2/2009 | Owa et al. |
| 2009/0060873 A1 | 3/2009 | Sporn et al. |
| 2009/0176827 A1 | 7/2009 | Lu et al. |
| 2009/0246198 A1 | 10/2009 | Dong et al. |
| 2009/0297519 A1 | 12/2009 | Moore et al. |
| 2009/0306101 A1 | 12/2009 | Solca et al. |
| 2009/0312360 A1 | 12/2009 | Zacharchuk |
| 2009/0317456 A1 | 12/2009 | Karrasch et al. |
| 2009/0318480 A1 | 12/2009 | Solca |
| 2009/0325877 A1 | 12/2009 | Grunt et al. |
| 2010/0041904 A1 | 2/2010 | Jiang et al. |
| 2010/0048540 A1 | 2/2010 | Boyle et al. |
| 2010/0048892 A1 | 2/2010 | Anderson et al. |
| 2010/0056777 A1 | 3/2010 | Anderson et al. |
| 2010/0069340 A1 | 3/2010 | Zacharchuk et al. |
| 2010/0081632 A1 | 4/2010 | Oksenberg et al. |
| 2010/0087482 A1 | 4/2010 | Haber et al. |
| 2010/0092490 A1 | 4/2010 | Uenaka et al. |
| 2010/0105031 A1 | 4/2010 | Matsui et al. |
| 2010/0113474 A1 | 5/2010 | Zacharhuk et al. |
| 2010/0120072 A1 | 5/2010 | Lorence et al. |
| 2010/0120768 A1 | 5/2010 | Steinberg et al. |
| 2010/0143340 A1 | 6/2010 | Kolhe et al. |
| 2010/0143350 A1 | 6/2010 | Green et al. |
| 2010/0166744 A1 | 7/2010 | Wong |
| 2010/0189773 A1 | 7/2010 | Mortimore et al. |
| 2010/0297118 A1 | 11/2010 | Macdougall et al. |
| 2010/0298760 A1 | 11/2010 | Olle et al. |
| 2010/0310503 A1 | 12/2010 | Li et al. |
| 2011/0014117 A1 | 1/2011 | Wang et al. |
| 2011/0045459 A1 | 2/2011 | Mischel et al. |
| 2011/0052570 A1 | 3/2011 | Klagsbrun et al. |
| 2011/0091421 A1 | 4/2011 | Mann |
| 2011/0091524 A1 | 4/2011 | Wang et al. |
| 2011/0097340 A1 | 4/2011 | Ramachandra et al. |
| 2011/0104256 A1 | 5/2011 | Wang et al. |
| 2011/0111018 A1 | 5/2011 | Ashraf et al. |
| 2011/0129456 A1 | 6/2011 | Wang et al. |
| 2011/0165257 A1 | 7/2011 | Rao et al. |
| 2012/0270896 A1 | 10/2012 | Zacharchuk |
| 2012/0308560 A1 | 12/2012 | Moore et al. |
| 2013/0189274 A1 | 7/2013 | Berkenblit et al. |
| 2013/0281488 A1 | 10/2013 | Lu et al. |
| 2014/0004203 A1 | 1/2014 | Rao et al. |
| 2014/0050721 A1 | 2/2014 | Moore et al. |
| 2014/0171384 A1 | 6/2014 | Zacharchuk et al. |

FOREIGN PATENT DOCUMENTS

| | | |
|---|---|---|
| WO | WO 02/080975 A1 | 10/2002 |
| WO | WO 02/098416 A2 | 12/2002 |
| WO | WO 03/050090 A1 | 6/2003 |
| WO | WO 03/103676 A2 | 12/2003 |
| WO | 2004004644 A2 | 1/2004 |
| WO | WO 2004/066919 A2 | 8/2004 |
| WO | WO 2004/078133 A2 | 9/2004 |
| WO | WO 2004/093854 A2 | 11/2004 |
| WO | WO 2005/018677 A2 | 3/2005 |
| WO | WO 2005/032513 A1 | 4/2005 |
| WO | WO 2005/034955 A1 | 4/2005 |
| WO | WO 2005/037287 A1 | 4/2005 |
| WO | WO 2005/044091 A2 | 5/2005 |
| WO | WO 2005/087265 A1 | 9/2005 |
| WO | WO 2005/094357 A2 | 10/2005 |
| WO | 2006044453 A1 | 4/2006 |
| WO | WO 2006/044748 A2 | 4/2006 |
| WO | WO 2006/081985 A1 | 8/2006 |
| WO | WO 2006/084058 A2 | 8/2006 |
| WO | 2006095185 A1 | 9/2006 |
| WO | WO 2006/098978 A1 | 9/2006 |
| WO | 2006113151 A2 | 10/2006 |
| WO | WO 2006/116514 A2 | 11/2006 |
| WO | WO 2006/120557 A1 | 11/2006 |
| WO | WO 2006/120573 A1 | 11/2006 |
| WO | WO 2006/127205 A2 | 11/2006 |
| WO | WO 2006/127207 A1 | 11/2006 |
| WO | WO 2007/000234 A1 | 1/2007 |
| WO | WO 2007/011619 A2 | 1/2007 |
| WO | 2007056118 A1 | 5/2007 |
| WO | WO 2007/075794 A2 | 7/2007 |
| WO | WO 2007/095038 A2 | 8/2007 |
| WO | WO 2007/130438 A2 | 11/2007 |
| WO | WO 2007/137187 A2 | 11/2007 |
| WO | WO 2007/139797 A2 | 12/2007 |
| WO | WO 2008/076278 A2 | 6/2008 |
| WO | WO 2008/089087 A2 | 7/2008 |
| WO | WO 2008/093878 A1 | 8/2008 |
| WO | WO 2008/121467 A2 | 10/2008 |
| WO | WO 2008/127710 A2 | 10/2008 |
| WO | WO 2008/130910 A1 | 10/2008 |
| WO | WO 2009/042613 A1 | 4/2009 |
| WO | WO 2009/052264 A2 | 4/2009 |
| WO | WO 2009/061349 A1 | 5/2009 |
| WO | WO 2009/105234 A2 | 8/2009 |
| WO | WO 2009/108637 A1 | 9/2009 |
| WO | WO 2009/111073 A2 | 9/2009 |
| WO | WO 2009/121031 A1 | 10/2009 |
| WO | WO 2009/126662 A1 | 10/2009 |
| WO | WO 2009/129545 A1 | 10/2009 |
| WO | WO 2009/129546 A1 | 10/2009 |
| WO | WO 2009/129548 A1 | 10/2009 |
| WO | WO 2009/146216 A2 | 12/2009 |
| WO | WO 2009/146218 A2 | 12/2009 |
| WO | WO 2009/151910 A2 | 12/2009 |
| WO | WO 2010/008744 A2 | 1/2010 |
| WO | WO 2010/011782 A1 | 1/2010 |
| WO | WO 2010/045318 A2 | 4/2010 |
| WO | WO 2010/048477 A2 | 4/2010 |
| WO | WO 2010/054051 A1 | 5/2010 |
| WO | WO 2010/085845 A1 | 8/2010 |
| WO | WO 2010/091140 A1 | 8/2010 |
| WO | WO 2010/098627 A2 | 9/2010 |
| WO | WO 2010/104406 A1 | 9/2010 |
| WO | WO 2010/117633 A1 | 10/2010 |
| WO | WO 2010/120861 A1 | 10/2010 |
| WO | WO 2010/124009 A2 | 10/2010 |
| WO | WO 2010/129053 A2 | 11/2010 |
| WO | WO 2011/002857 A2 | 1/2011 |
| WO | WO 2011/008053 A1 | 1/2011 |
| WO | WO 2011/008054 A2 | 1/2011 |
| WO | WO 2011/025267 A2 | 3/2011 |
| WO | WO 2011/025269 A2 | 3/2011 |
| WO | WO 2011/025271 A2 | 3/2011 |
| WO | WO 2011/038467 A1 | 4/2011 |
| WO | WO 2011/056741 A2 | 5/2011 |

(56) References Cited

FOREIGN PATENT DOCUMENTS

| WO | WO 2011/060206 A2 | 5/2011 |
|----|-------------------|--------|
| WO | WO 2011/069962 A1 | 6/2011 |
| WO | WO 2011/070499 A1 | 6/2011 |

OTHER PUBLICATIONS

Scaltriti et al. (J. Natl. Cancer Inst. 2007, 99:628-638).*
Stockier et al. (Breast Cancer Research and Treatment 2003, 81:S49-S52).*
Burstein, New England Journal of Medicine 2005 (353) 1652-1654.*
Wong et al. (Clin. Cancer Res. 2009, 15:2552-2558).*
Bedard L et al., "Beyond Trastuzumab: overcoming resistance to targeted HER-2 therapy in breast cancer," Current Cancer Drug Targets, 2009, 9(2), 148-162.
Burstein et al., "HKI-272, an irreversible pan erbB receptor tyrosine kinase inhibitor: preliminary phase 2 results in patients with advanced breast cancer," Breast Cancer Research and Treatment, 2007, 106, S268.
Cho et al., "Structure of the extracellular region of HER2 alone and in complex with the Herceptin Fab," Nature, 2003, 421, 756-760.
Cox, "Regression models and life tables (with discussion)," Journal of the Royal Statistical Society, 1972, Series B, 34, 187-220.
World Health Statistics, 2008, World Health Organization.
Iliadis et al., "APIS: a software for model identification, simulation and dosage regimen calculations in clinical and experimental pharmacokinetics," Computer Methods and Programs in Biomedicine, 1992, 38, 227-239.
Jelliffe et al., "Adaptive control of drug dosage regimens: basic foundations, relevant issues, and clinical examples," Int. J. Biomed. Comput., 1994, 36, 1-23.
Kaplan and Meier, "Nonparametric estimation from incomplete observations," J. Am. Stat. Assoc., 1958, 53, 457-481.
Ligibel and Winer, "Trastuzumab/chemotherapy combinations in metastatic breast cancer," Seminars in Oncology, 2002, 29(3 Suppl 11), 38-43.
Mantel and Haenszel, "Statistical aspects of the analysis of data from retrospective studies of disease," J. Nat. Cancer Inst., 1959, 22, 719-48.
Parkin and Fernandez, "Use of statistics to assess the global burden of breast cancer," Breast Journal, 2006, 12 (Suppl. 1), S70-80.
Perez et al., "Updated results of the combined analysis of NCCTG N9831 and NSABP B-31 adjuvant chemotherapy with/without trastuzumab in patients with HER2-positive breast cancer," Journal of Clinical Oncology, ASCO Annual Meeting Proceedings, 2007, 25(18S), 512.
Rabindran et al., "Antitumor activity of HKI-272, an orally active, irreversible inhibitor of the HER-2 tyrosine kinase," Cancer Research, 2004, 64(11), 3958-3965.
Slamon, "Human breast cancer: correlation of relapse and survival with amplification of the HER-2/neu oncogene," Science, 1987, 235, 177-182.
Slamon et al., "2nd Interim analysis phase III randomized trial comparing doxorubicin and cyclophosphamide followed by docetaxel (AC T) with doxorubicin and cyclophosphamide followed by docetaxel and trastuzumab (AC TH) with docetaxel, carboplatin and trastuzumab (TCH) in Her2neu positive early breast cancer patients," SABCC, BCIRG 006, 2006.
Smith et al., "2-Year follow-up of Trastuzumab after adjuvant chemotherapy in HER2-positive breast cancer: a randomized controlled trial," Lancet, 2007, 369, 29-36.
Widakowich et al., "HER-2 positive breast cancer: what else beyond Trastuzumab-based therapy?" Anti-Cancer Agents in Medicinal Chemistry, 2008, 8(5), 488-496.
Wissner et al., "The development of HKI-272 and related compounds for the treatment of cancer," Arch. Pharm. Chem. Life Sci., 2008, 341, 465-477.
Wong et al., "A phase I study with Neratinib (HKI-272), an irreversible pan ErbB receptor tyrosine kinase inhibitor, in patients with solid tumors," Clin. Cancer Res., 2009, 15(7), 2552-2558.

World Health Organization Fact Sheet, No. 297, 2008.
Zagrekova et al, Drug Treatment of Breast Cancer, Rossijskij medicinskij zhurnal, 2002, 14, 605 (partial English translation).
Zhao et al. "Neratinib reverses ATP-binding cassette B1-mediaed chemotherapeutic drug resistance in vitro, in vivo, and ex-vivo," Mol. Pharmacol, 82: 47-58 (2012).
Goldhirsch et al., "2 years versus 1 year of adjuvant trastuzumab for HER2-positive breast cancer (HERA): an open-label, randomised controll trial," Lancet, 382:1021-1028 (2013).
Ross et al., "The HER-2 receptor and breast cancer: ten years of targeted anti-HER-2 therapy and personalized medicine," The Oncologist, 14:320-368 (2009).
Lou et al., "Progress in target therapy for breast cancer," J. Oncology, (2009),15:788-795 (English abstract).
Ershler, "Capecitabine monotherapy: safe and effective treatment for metastatic breast cancer," Oncologist 11 (4):325-335 (2006).
Hudis et al., "Proposal for standardized definitions for efficacy end points in adjuvant breast cancer trials: the STEEP system," J. Clin. Oncol. 25(15):2127-2132 (2007).
Iwase, "Current topics and perspectives on the use of aromatase inhibitors in the treatment of breast cancer," Breast Cancer 15(4):278-290 (2008) (Epub Sep. 23, 2008).
Kaklamani and Gradishar, "Capecitabine: treatment options in metastatic breast cancer," Expert Rev. Obstet. Gynecol. 4(4):367-376 (2009).
Mamounas et al. "Benefit from exemestane as extended adjuvant therapy after 5 years of adjuvant tamoxifen: intention-to-treat analysis of the National Surgical Adjuvant Breast and Bowel Project B-33 trial," J. Clin. Oncol. 26 (12):1965-1971 (2008) (Epub Mar. 10. 2008).
McArthur and Hudis, "Updates in adjuvant systemic treatment of breast cancer," Update Cancer Ther. 2:193-199 (2007).
Muss et al., "Adjuvant chemotherapy in older women with early-stage breast cancer," N. Engl. J. Med. 2009, 360 (20):2055-2065 (2009).
Saarto, "Adjuvant therapy of breast cancer—bisphosphonates," Cancer Treat. Res. 151:163-177 (2009).
"Trastuzumab." Wikipedia: Wikipedia: The Free Encyclopedia. Wikimedia Foundation, Inc. Retrieved from the Internet Aug. 14, 2009. URL:http://en.wikipedia.org/wiki/Herceptin.
Abbas et al., "A Drug Interaction Study to Evaluate the Effect of Ketoconazole on the Pharmacokinetics (PK) of Neratinib in Healthy Subjects," Clin. Pharmacol. Therapeutics 85:s44 (2009).
Abbas et al., "Evaluation of Neratinib (HKI-272) and Paclitaxel Pharmacokinetics (PK) in Asian and Caucasian Patients with Erbb2+ Breast Cancer: a Phase 1/2 Study of Neratinib in Combination with Paclitaxel," Ann. Oncol. 21:101 (2010).
Abbas et al., "Pharmacokinetics of Oral Neratinib During Co-Administration of Ketoconazole in Healthy Subjects," Br. J. Clin. Pharmacol. 71(4):522-527 (2011).
Abbas-Borhan et al., "A Clinical Study to Characterize the Occurrence of Mild-To-Moderate Diarrhea After Administration of Neratinib Either Once Daily or Twice Daily for 14 Days," EJC Suppl. 8:143 (2010).
Abbas-Borhan et al., "An Open-Label Study to Assess the Mass Balance and Metabolic Disposition of an Orally Administered Single Dose of 14C-Labeled Neratinib, an Irreversible pan-ErbB inhibitor, in Healthy Subjects," Drug Metab. Rev. 42:S1, 216 Abstr. P330 (2010).
Abrams et al., "Preclinical evaluation of the tyrosine kinase inhibitor SU11248 as a single agent and in combination with "standard of care" therapeutic agents for the treatment of breast cancer," Mol. Cancer Ther. 2(10):1011-1021 (2003).
Abramson and Arteaga, "New Strategies in HER2-Overexpressing Breast Cancer: Many Combinations of Targeted Drugs Available," Clin. Cancer Res. 17:952-958 (2011).
Adelaide et al., "Integrated Profiling of Basal and Luminal Breast Cancers," Cancer Res. 67(24):11565-11575 (2007).
Al-Dasooqi et al., "HER2 Targeted Therapies for Cancer and the Gastrointestinal Tract," Curr. Drug Targets 10(6):537-542 (2009).
Ali et al., "Mutational Spectra of PTEN/MMAC1 Gene: a Tumor Suppressor with Lipid Phosphatase Activity," J. Natl. Cancer Inst. 91(22):1922-1932 (1999).

(56) References Cited

OTHER PUBLICATIONS

Allegra et al., "American Society of Clinical Oncology Provisional Clinical Opinion: Testing for KRAS Gene Mutations in Patients With Metastatic Colorectal Carcinoma to Predict Response to Anti-Epidermal Growth Factor Receptor Monoclonal Antibody Therapy," J. Clin. Oncol. 27(12):2091-2096 (2009).
Alvarez et al., "Emerging Targeted Therapies for Breast Cancer," J. Clin. Oncol. 28(20):3366-3379 (2010).
Álvarez, "Present and Future Evolution of Advanced Breast Cancer Therapy," Breast Cancer Res. 12(Suppl 2):S1 (2010).
Amslinger, "The tunable functionality of alpha,beta-unsaturated carbonyl compounds enables their differential application in biological systems," ChemMedChem. 5(3):351-356 (2010).
Andre and Diniz, "Targeted regimes without cytotoxics—are they ready for prime time?" EJC Suppl. 7:49 Abst. 191 (2009).
Anonymous: "Meeting Archives of Chemotherapy Foundation Symposium XXIV, Nov. 7-10, 2007", The Chemotherapy Foundation, Nov. 8, 2007, Retrieved from the Internet on Jan. 13, 2010: URL:http://www.chemotherapyfoundationsymposium.org/meeting_archives/meetingarchives_tcf2007_main.html.
Anonymous: "Anticancer Agent—neratinib", Manufacturing Chemist, Dec. 2010/Jan. 2011, p. 27.
Arteaga, "ErbB-targeted therapeutic approaches in human cancer," Exp. Cell. Res. 284(1):122-130 (2003).
Awada and Piccart-Gebhart, "Management of HER-2/Neu-Positive Metastatic Breast Cancer," Eur. J. Cancer (Suppl. 6):2-9 (2008).
Awada et al., "Safety and Efficacy of Neratinib (HKI-272) in Combination with Vinorelbine in ErbB2+ Metastatic Breast Cancer," Cancer Res. 69:24(Suppl 3) Abstr. 5095 (2009).
Awada et al., "Safety and Efficacy of Neratinib (HKI-272) in Combination with Vinorelbine in ErbB2+ Metastatic Breast Cancer (MBC)," Ann. Oncol. 21(Suppl. 4):iv62-iv63 Abstr. 145P (2010).
Azria et al., "[Radiotherapy and inhibitors of epidermal growth factor receptor: preclinical findings and preliminary clinical trials]," Bull Cancer. 90 Spec No. S202-S212 (2003). (Abstract only).
Badache and Goncalves, "The ErbB2 signaling network as a target for breast cancer therapy," J. Mammary Gland Biol. Neoplasia 11(1):13-25 (2006).
Barton et al., "Predictive molecular markers of response to epidermal growth factor receptor(EGFR) family-targeted therapies," Curr. Cancer Drug Targets 10(8):799-812 (2010).
Baselga and Swain, "Novel anticancer targets: revisiting ERBB2 and discovering ERBB3," Nat. Rev. Cancer 9(7):463-475 (2009) (Epub Jun. 18, 2009).
Baselga, "Is there a role for the irreversible epidermal growth factor receptor inhibitor EKB-569 in the treatment of cancer? A mutation-driven question," J. Clin. Oncol. 24(15):2225-2226 (2006).
Baselga, "Novel agents in the era of targeted therapy: what have we learned and how has our practice changed?" Ann. Oncol. 19(Suppl 7):vii281-vii288 (2008).
Baselga, "Treatment of HER2-Overexpressing Breast Cancer," Ann. Oncol. (Suppl 7):vii36-vii40 (2010).
Bayes et al., "Gateways to clinical trials," Methods Find. Exp. Clin. Pharmacol. 28(9):657-678 (2006).
Bedard et al., "Stemming resistance to HER-2 targeted therapy," J. Mammary Gland Biol. Neoplasia 14(1):55-66 (2009) (Epub Mar. 4, 2009).
Belani, "The role of irreversible EGFR inhibitors in the treatment of non-small cell lung cancer: overcoming resistance to reversible EGFR inhibitors," Cancer Invest. 28(4):413-423 (2010).
Bell and Haber, "A blood-based test for epidermal growth factor receptor mutations in lung cancer," Clin. Cancer Res. 12(13):3875-3877 (2006).
Berns et al., "A functional genetic approach identifies the PI3K pathway as a major determinant of trastuzumab resistance in breast cancer," Cancer Cell 12(4):395-402 (2007).
Berz and Wanebo, "Targeting the growth factors and angiogenesis pathways: small molecules in solid tumors," J. Surg. Oncol. 103(6):574-586 (2011).

Besse et al., "Neratinib (HKI-272), an irreversible pan-ErbB receptor tyrosine kinase inhibitor: preliminary results of a phase 2 trial in patients with advanced non-small cell lung cancer," Eur. J. Cancer (Suppl.):23 Abstr. 203 (2008).
Besse et al., "Targeted therapies in lung cancer," Ann. Oncol. 18(Suppl. 9):ix135-ix142 (2007).
Bettendorf et al., "Chromosomal imbalances, loss of heterozygosity, and immunohistochemical expression of TP53, RB1, and PTEN in intraductal cancer, intraepithelial neoplasia, and invasive adenocarcinoma of the prostate," Genes Chromosomes Cancer 47(7):565-572 (2008).
Bischoff and Ignatov, "The Role of Targeted Agents in the Treatment of Metastatic Breast Cancer," Breast Care (Basel) 5(3):134-141 (2010) (Epub Jun. 16, 2010).
Blanco-Aparicio et al., "PTEN, More Than the AKT Pathway," Carcinogenesis 28(7):1379-1386 (2007) (Epub Mar. 6, 2007).
Blencke et al., "Mutation of threonine 766 in the epidermal growth factor receptor reveals a hotspot for resistance formation against selective tyrosine kinase inhibitors," J. Biol. Chem. 278(17):15435-15440 (2003) (Epub Feb. 19, 2003).
Board et al., "Multiplexed assays for detection of mutations in PIK3CA," Clin. Chem 54(4):757-760 (2008).
Bonanno et al., "Mechanisms of acquired resistance to epidermal growth factor receptor tyrosine kinase inhibitors and new therapeutic perspectives in non small cell lung cancer," Curr. Drug Targets 12(6):922-933 (2011).
Boschelli, "4-Anilino-3-quinolinecarbonitriles: An Emerging Class of Kinase Inhibitors—An Update," Med. Chem Rev. Online 1:457-463 (2004).
Bose and Ozer, "Neratinib: an oral, irreversible dual EGFR/HER2 inhibitor for breast and non-small cell lung cancer," Expert Opin. Investig. Drugs 18(11):1735-1751 (2009).
Bose et al., "Allelic loss of chromosome 10q23 is associated with tumor progression in breast carcinomas," Oncogene 17(1):123-127 (1998).
Bose et al., "Reduced expression of PTEN correlates with breast cancer progression," Hum. Pathol. 33(4):405-409 (2002).
Boyce et al., "Requirement of pp60c-src expression for osteoclasts to form ruffled borders and resorb bone in mice," J. Clin. Invest. 90(4):1622-1627 (1992).
Boyd et al., "Lapatanib: Oncolytic Dual EFGR and erbB-2 Inhibitor," Drugs Future 30(12):1225-1239 (2005).
Brackstone et al., "Canadian initiatives for locally advanced breast cancer research and treatment: inaugural meeting of the Canadian Consortium for LABC," Curr. Oncol. 18(3):139-144 (2011).
Bridges, "Current Progress Towards the Development of Tyrosine Kinase Inhibitors as Anticancer Agents," Expert Opin. Emerg. Drugs. 3:279-292 (1998).
Brittain, Harry G. (Eds), "Polymorphism in Pharmaceutical Solids", Chapters 1 and 5, Marcel Dekker, Inc., New York (1999).
Brook et al., "Management of transitional cell carcinoma by targeting the epidermal growth factor receptor," Therapy 3(3):407-416 (2006).
Browne et al., "HER-2 Signaling and Inhibition in Breast Cancer," Curr. Cancer Drug Targets 9(3):419-438 (2009).
Broxterman and Georgopapadakou, "Anticancer therapeutics: a surge of new developments increasing target tumor and stroma," Drug Resist. Updat. 10(4-5):182-193 (2007) (Epub Sep. 12, 2007).
Buerger et al., "Allelic length of a CA dinucleotide repeat in the egfr gene correlates with the frequency of amplifications of this sequence—first results of an inter-ethnic breast cancer study," J. Pathol. 203(1):545-550 (2004).
Bullard Dunn et al., "Evolving Therapies and FAK Inhibitors for the Treatment of Cancer," Anticancer Agents Med. Chem. 10(10):722-734 (2010).
Burstein et al., "Gastrointestinal and Cardiovascular Safety Profiles of Neratinib Monotherapy in Patients with Advanced Erbb2-Positive Breast Cancer," Cancer Res. 69:Abst 5096 (2009).
Burstein et al., "Neratinib (HKI-272), an irreversible pan ErbB receptor tyrosine kinase inhibitor: phase 2 results in patients with advanced HER2+ breast cancer," Cancer Res. 69(2 Suppl.) Abstr. 37 (2009).
Burstein et al., "Neratinib, an irreversible ErbB receptor tyrosine kinase inhibitor, in patients with advanced ErbB2-positive breast cancer," J. Clin. Oncol. 28(8):1301-1307 (2010).

(56) References Cited

OTHER PUBLICATIONS

Byrn et al., "Pharmaceutical solids: a strategic approach to regulatory considerations," Pharm. Res. 12(7):945-954 (1995).
Callahan and Hurwitz, "Human epidermal growth factor receptor-2-positive breast cancer: Current management of early, advanced, and recurrent disease," Curr. Opin. Obstet. Gynecol. 23(1):37-43 (2011).
Camp et al., "Molecular mechanisms of resistance to therapies targeting the epidermal growth factor receptor," Clin. Cancer Res. 11(1):397-405 (2005).
Campas et al., "BIBW-2992. Dual EGFR/HER2 Inhibitor Oncolytic;Tovok™," Drugs Future 33(8):649-654 (2008).
Campbel et al., "Gefitinib for the Treatment of Non-Small-Cell Lung Cancer," Expert Opin. Pharmacother. 11(8):1343-1357 (2010).
Cao et al., "Epidermal Growth Factor Receptor as a Target for Anti-Cancer Agent Design," Anticancer Agents Med. Chem. 10(6):491-503 (2010).
Cappuzzo et al., "Surrogate predictive biomarkers for response to anti-EGFR agents: state of the art and challenges," Int. J. Biol. Markers 22(1 Suppl 4):S10-23 (2007).
Cardoso et al., "Locally Recurrent or Metastatic Breast Cancer: ESMO Clinical Practice Guidelines for Diagnosis, Treatment and Follow-Up," Ann. Oncol. 21(5):v15-v19 (2010).
Carney et al., "HER-2/neu diagnostics in breast cancer," Breast Cancer Res. 9(3):207 (2007).
Carter et al., "Small-Molecule Inhibitors of the Human Epidermal Receptor Family," Expert Opin. Investig. Drugs 18(12):1829-1842 (2009).
Cascone et al., "Epidermal Growth Factor Receptor Inhibitors in Non-Small-Cell Lung Cancer," Expert Opin. Drug Discov. 2(3):335-348 (2007).
Chan and Giaccia, "Harnessing Synthetic Lethal Interactions in Anticancer Drug Discovery," Nat. Rev. Drug Discov. 10(5):351-364 (2011).
Chandrasekaran et al., "Reversible Covalent Binding of Neratinib to Human Serum Albumin in Vitro," Drug Metab. Left. 4(4):220-227 (2010).
Chen et al., "Epidermal growth factor receptor inhibitors: current status and future directions," Curr. Probl. Cancer 33(4):245-294 (2009).
Chenoweth, "Can single-patient investigational new drug studies hurry slow trains to the fast track?" Drug Discov. Today 11(5-6):185-186 (2006).
Cheung and Paterson, "American Chemical Society—226th National Meeting. Pain and Oncology," Idrugs 6(10):935-936 (2003).
Chien and Rugo, "The Cardiac Safety of Trastuzumab in the Treatment of Breast Cancer," Expert Opin. Drug Saf. 9(2):335-346 (2010).
Chow et al., "Safety and efficacy of neratinib (HKI-272) in combination with paclitaxel in ErbB2+ metastatic breast cancer," Cancer Res. (Meeting Abstracts) 69:S5081 (2009).
Chow et al., "Safety and efficacy of neratinib (HKI-272) in combination with paclitaxel in patients with solid tumors," J. Clin. Oncol. (Meeting Abstracts) 27(155):3557 (2009).
Chow et al., "Safety and efficacy of neratinib (HKI-272) in combination with paclitaxel in ERBB2+ metastatic breast cancer (MBC)," Ann. Oncol. 21(Suppl 4):iv62 Abstr. 144P (2010).
Cicenas, "The Potential Role of the EGFR/ERBB2 Heterodimer in Breast Cancer," Expert Opin. Ther. Patents 17(6):607-616 (2007).
Clouser et al., "Biomarker Targets and Novel Therapeutics," Cancer Treat. Res. 149:85-105 (2009).
Cobleigh et al., "Multinational study of the efficacy and safety of humanized anti-HER2 monoclonal antibody in women who have HER2-overexpressing metastatic breast cancer that has progressed after chemotherapy for metastatic disease," J. Clin. Oncol. 17(9):2639-2648 (1999).
Collins et al., "Lapatinib: a competitor or companion to trastuzumab?" Cancer Treat. Rev. 35(7):574-581 (2009).
Colombo et al., "HER2 targeting as a two-sided strategy for breast cancer diagnosis and treatment: Outlook and recent implications in nanomedical approaches," Pharmacol. Res. 62(2):150-165 (2010) (Epub Feb. 1, 2010).

Cooper and Cohen, "Mechanisms of resistance to EGFR inhibitors in head and neck cancer," Head Neck 31(8):1086-1094 (2009).
Cortes-Funes et al., "Neratinib, An Irreversible Pan Erb Receptor Tyrosine Kinase Inhibitor Active for Advanced HER2+ Breast Cancer," Breast Cancer Res. 11 Suppl 1:S19 (2009).
Coughlin et al., "Approaches and limitations of phosphatidylinositol-3-kinase pathway activation status as a predictive biomarker in the clinical development of targeted therapy," Breast Cancer Res. Treat. 124(1):1-11 (2010) (Epub Aug. 28, 2010).
Da Cunha Santos et al., "EGFR Mutations and Lung Cancer," Ann. Rev. Pathol. 6:49-69 (2011).
Damia and D'Incalci, "Contemporary pre-clinical development of anticancer agents—what are the optimal preclinical models?" Eur. J. Cancer 45(16):2768-2781 (2009) (Epub Sep. 15, 2009).
Dancey, "Epidermal growth factor receptor inhibitors in non-small cell lung cancer," Drugs 67(8):1125-1138 (2007).
Dang et al.,"The safety of dose-dense doxorubicin and cyclophosphamide followed by paclitaxel with trastuzumab in HER-2/neu overexpressed/amplified breast cancer," J. Clin. Oncol. 26(8):1216-1222 (2008).
Daniele and Sapino, "Anti-HER2 treatment and breast cancer: state of the art, recent patents, and new strategies," Recent Pat. Anticancer Drug Discov. 4(1):9-18 (2009).
Davidson, "HER2-Targeted Therapies: How Far We've Come-And Where We're Headed," Oncology (Williston Park) 25(5):425-426 (2011).
Davoli et al., "Progression and Treatment of HER2-Positive Breast Cancer," Cancer Chemother. Pharmacol. 65(4):611-623 (2010) (Epub Dec. 20, 2009).
De Bono and Rowinsky, "The ErbB receptor family: a therapeutic target for cancer," Trends Mol. Med. 8(4 Suppl):S19-S26 (2002).
De Luca and Normanno, "Predictive biomarkers to tyrosine kinase inhibitors for the epidermal growth factor receptor in non-small-cell lung cancer," Curr. Drug Targets 11(7):851-864 (2010).
De Seranno and Meuwissen, "Progress and Applications of Mouse Models for Human Lung Cancer," Eur. Respir. J. 5(2):426-443 (2010).
Depowski et al., "Loss of expression of the PTEN gene protein product is associated with poor outcome in breast cancer," Mod. Pathol. 14(7):672-676 (2001).
Di Cosimo and Baselga, "Management of breast cancer with targeted agents: importance of heterogeneity. [corrected]." Nat. Rev. Clin. Oncol. 7(3):139-147 (2010) (Epub Feb. 2, 2010).
Di Cosimo and Baselga, "Targeted Therapies in Breast Cancer: Where Are We Now?" Eur. J. Cancer 44(18):2781-2790 (2008) (Epub Nov. 14, 2008).
Di Maio et al., "New drugs in advanced non-small-cell lung cancer: searching for the correct clinical development," Expert Opin. Investig. Drugs 19(12):1503-1514 (2010) (Epub Nov. 4, 2010).
Dickler, "Updates on Therapeutic Approaches in HER2-Positive Disease," Clin. Adv. Hematol. Oncol. 8(2):105-107 (2010).
Dinh et al., "Trastuzumab for early breast cancer: current status and future directions," Clin. Adv. Hematol. Oncol. 5(9):707-717 (2007).
Dirix et al., "Neratinib Monotherapy in Patients with Advanced ERBB2-Positive Breast Cancer: Gastrointestinal and Cardiovascular Safety Profiles," Ann. Oncol. 21(Suppl 4):iv61-iv62 Abstr. 141P (2010).
Doebele et al., "New strategies to overcome limitations of reversible EGFR tyrosine kinase inhibitor therapy in non-small cell lung cancer," Lung Cancer 69(1):1-12 (2010) (Epub Jan. 25, 2010).
Dorland's Illustrated Medical Dictionary. 31st ed. Philadelphia: Saunders Elsevier; c2007. Carcinoma; pp. 295-297.
Dowsett and Dunbier, "Emerging Biomarkers and New Understanding of Traditional Markers in Personalized Therapy for Breast Cancer," Clin. Cancer Res. 14(24):8019-8026 (2008).
Eck and Yun, "Structural and Mechanistic Underpinnings of the Differential Drug Sensitivity of EGFR Mutations in Non-Small Cell Lung Cancer," Biochim. Biophys. Acta 1804(3):559-566 (2010).
Egloff and Grandis, "Targeting epidermal growth factor receptor and SRC pathways in head and neck cancer," Semin. Oncol. 35(3):286-297 (2008).

(56) References Cited

OTHER PUBLICATIONS

Einhorn et al., "Summary Report 7th Annual Targeted Therapies of the Treatment of Lung Cancer," J. Thorac. Oncol. 3(5):545-555 (2008).
Einhorn, "Perspective on the Development of New Agents in Thoracic Cancers," Lung Cancer 50 Suppl 1:S27-S28 (2005).
Ellis and Crowder, "PIKing" the winner for phosphatidylinositol 3-kinase inhibitors in ErbB2-positive breast cancer: let's not "PTENed" it's easy! Clin. Cancer Res. 13(19):5661-5662 (2007).
Engelman and Settleman, "Acquired Resistance to Tyrosine Kinase Inhibitors During Cancer Therapy," Curr. Opin. Genet. Dev. 18(1):73-79 (2008) (Epub Mar. 5, 2008).
Engelman, "Targeting PI3K Signalling in Cancer: Opportunities, Challenges and Limitations," Nat. Rev. Cancer 9(8):550-562 (2009).
Engleman and Jänne, "Mechanisms of acquired resistance to epidermal growth factor receptor tyrosine kinase inhibitors in non-small cell lung cancer," Clin. Cancer Res. 14(10):2895-2899 (2008).
Ercan et al., "Amplification of EGFR T790M causes resistance to an irreversible EGFR inhibitor," Oncogene. 29(16):2346-2356 (2010) (Epub Feb. 1, 2010).
Esteva et al., "Molecular predictors of response to trastuzumab and lapatinib in breast cancer," Nat. Rev. Clin. Oncol. 7(2):98-107 (2010) (Epub Dec. 22, 2009).
Farley and Birrer, "Novel Therapeutic Targets," Cancer Treat. Res. 149:63-84 (2009).
Felip et al., "Emerging Drugs for Non-Small-Cell Lung Cancer," Expert Opin. Emerg. Drugs 12(3):449-460 (2007).
Ferron et al., "Oral bioavailability of pantoprazole suspended in sodium bicarbonate solution," Am. J. Health Syst. Pharm. 60(13):1324-1329 (2003).
Fertéet al., "Molecular circuits of solid tumors: prognostic and predictive tools for bedside use," Nat. Rev. Clin. Oncol. 7(7):367-380 (2010) (Epub Jun. 15, 2010).
Fleming et al., "Nitrile-containing pharmaceuticals: efficacious roles of the nitrile pharmacophore," J. Med. Chem. 53(22)7902-7917 (2010) (Epub Aug. 30, 2010).
Folkman, "Angiogenesis in cancer, vascular, rheumatoid and other disease," Nat. Med. 1(1):27-31 (1995).
Früh, "The search for improved systemic therapy of non-small cell lung cancer—what are today's options?" Lung Cancer 72(3):265-270 (2011) (Epub Apr. 14, 2011).
Fry, "Inhibition of the epidermal growth factor receptor family of tyrosine kinases as an approach to cancer chemotherapy: progression from reversible to irreversible inhibitors," Pharmacol. Ther. 82(2-3):207-218 (1999).
Gadji et al., "EGF receptor inhibitors in the treatment of glioblastoma multiform: old clinical allies and newly emerging therapeutic concepts," Eur. J. Pharmacol. 625(1-3):23-30 (2009) (Epub Oct. 18, 2009).
Gajria and Chandarlapaty, "HER2-amplified breast cancer: mechanisms of trastuzumab resistance and novel targeted therapies," Expert Rev. Anticancer Ther. 11(2):263-275 (2011).
Gajria et al., "Tolerability and Efficacy of Targeting Both mTOR and HER2 Signaling in Trastuzumab-Refractory HER2+ Metastatic Breast Cancer," San Antonio Breast cancer Symposium. Abstract P5-18-04 (2010).
Garcia et al., "Promoter Methylation of the PTEN Gene is a Common Molecular Change in Breast Cancer," Genes Chromosomes Cancer 41(2):117-127 (2004).
Garrett and Arteaga, "Resistance to HER2-directed antibodies and tyrosine kinase inhibitors: mechanisms and clinical implications," Cancer Biol. Ther. 11(9):793-800 (2011) (Epub May 1, 2011).
Gatzemeier, "Second-Generation EGFR Inhibitors and Combinations," J. Thorac Oncol. 4(9): S121 (2009).
Gazdar, "Activating and Resistance Mutations of EGFR in Non-Small-Cell Lung Cancer: Role in Clinical Response to EGFR Tyrosine Kinase Inhibitors," Oncogene 28:S24-S31 (2009).
Gennaro (Ed.), Remington's Pharmaceutical Sciences, 17th Edition, Alfonso R. Gennaro, Mack Publishing Company, Easton, PA (1985).
Geuna et al., "Hitting multiple targets in HER2-positive breast cancer: proof of principle or therapeutic opportunity?" Expert Opin. Pharmacother. 12(4):549-565 (2011) (Epub Jan. 6, 2011).
Geyer et al., "Lapatinib plus capecitabine for HER2-positive advanced breast cancer," N. Engl. J. Med. 355(26):2733-2743 (2006).
Ghayad and Cohen, "Inhibitors of the PI3K/Akt/mTOR pathway: new hope for breast cancer patients," Recent Pat. Anticancer Drug Discov. 5(1):29-57 (2010).
Giamas et al., "Kinases as Targets in the Treatment of Solid Tumors," Cell. Signal. 22(7):984-1002 (2010) (Epub Jan. 21, 2010).
Glaxosmithkline, Tykerb Prescription Label, 2010, pp. 1-25.
Glück, "Chemotherapy Regimens in Metastatic Breast Cancer," Clin. Adv. Hematol. Oncol. 9(1)47-48 (2011).
Godin-Heymann et al., "Oncogenic activity of epidermal growth factor receptor kinase mutant alleles is enhanced by the T790M drug resistance mutation," Cancer Res. 67(15):7319-7326 (2007).
Godin-Heymann et al., "The T790M "gatekeeper" mutation in EGFR mediates resistance to low concentrations of an irreversible EGFR inhibitor," Mol. Cancer Ther. 7(4):874-879 (2008).
Govindan, "A review of epidermal growth factor receptor/HER2 inhibitors in the treatment of patients with non-small-cell lung cancer," Clin. Lung Cancer 11(1):8-12 (2010).
Grimm et al., "Diagnostic and Therapeutic Use of Membrane Proteins in Cancer Cells," Curr. Med. Chem. 18(2):176-190 (2011).
Guarneri et al., "Anti-HER2 neoadjuvant and adjuvant therapies in HER2 positive breast cancer," Cancer Treat. Rev. 36 Suppl 3:S62-S66 (2010).
Gullick et al., "Expression of epidermal growth factor receptors on human cervical, ovarian, and vulval carcinomas," Cancer Res. 46(1):285-292 (1986).
Hager et al., "PTEN expression in renal cell carcinoma and oncocytoma and prognosis," Pathology 39(5):482-485 (2007) (Abstract Only).
Hammerman et al., "Resistance to Epidermal Growth Factor Receptor Tyrosine Kinase Inhibitors in Non-Small Cell Lung Cancer," Clin. Cancer Res. 15(24):7502-7509 (2009).
Harris et al., "c-erbB-2 in serum of patients with breast cancer," Int. J. Biol. Markers 14(1):8-15 (1999).
Hasselblatt, "Ependymal Tumors," Recent Results Cancer Res. 171:51-66 (2009).
Hawkins and Grunberg, "Chemotherapy-Induced Nausea and Vomiting: Challenges and Opportunities for Improved Patient Outcomes," Clin. J. Oncol. Nurs. 13(1):54-64 (2009).
Hegedus et al., "Interaction of ABC multidrug transporters with anticancer protein kinase inhibitors: substrates and/or inhibitors?" Curr. Cancer Drug Targets 9(3):252-272 (2009).
Heigener and Reck, "Mutations in the epidermal growth factor receptor gene in non-small cell lung cancer: Impact on treatment beyond gefitinib and erlotinib," Adv. Ther. 28(2):126-133 (2011) (Epub Dec. 16, 2010).
Heigener, "Non-Small Cell Lung Cancer in Never-Smokers: a New Disease Entity?" Onkologie 34(4):202-207 (2011) (Epub Mar. 18, 2011).
Heymach et al., "Epidermal growth factor receptor inhibitors in development for the treatment of non-small cell lung cancer," Clin. Cancer Res. 12(14 Pt 2):4441s-4445s (2006).
Higa et al., "Biological considerations and clinical applications of new HER2-targeted agents," Expert Rev. Anticancer Ther. 10(9):1497-1509 (2010).
Ho and Laskin, "EGFR-directed therapies to treat non-small-cell lung cancer," Expert Opin. Investig. Drugs 18(8):1133-1145 (2009).
Holbro and Hynes, "ErbB receptors: directing key signaling networks throughout life," Annu. Rev. Pharmacol. Toxicol. 44:195-217 (2004).
Holodov and Yakovlev, Clinical Pharmacokinetics, Moscow, Medicine, (1985), pp. 83-98, 134-138, 160, 378-380 (English translation not available).
Hookes and Lakeram, "American Chemical Society—235th National Meeting. Part 2: EGFR kinase inhibitors and β3-lactamases under investigation by Wyeth" Idrugs 11(6):391-393 (2008).

(56) References Cited

OTHER PUBLICATIONS

Horn and Sandler, "Epidermal growth factor receptor inhibitors and antiangiogenic agents for the treatment of non-small cell lung cancer," Clin. Cancer Res. 15(16):5040-5048 (2009) (Epub Aug. 11, 2009).
Hou and Kumamoto, "Flavonoids as protein kinase inhibitors for cancer chemoprevention: direct binding and molecular modeling," Antioxid. Redox Signal. 13(5):691-719 (2010).
Huang et al., "Up-regulation of miR-21 by HER2/neu signaling promotes cell invasion," J. Biol. Chem. 284(27):18515-18524 (2009) (Epub May 6, 2009).
Hubalek et al., "Resistance to HER2-targeted therapy: mechanisms of trastuzumab resistance and possible strategies to overcome unresponsiveness to treatment," Wien. Med. Wochenschr. 160(19-20):506-512 (2010) (Epub Oct. 26, 2010).
Huber et al., "Pharmacokinetics of pantoprazole in man," Int. J. Clin. Pharmacol. Ther. 34(5):185-194 (1996).
Hug et al., "A single-dose, crossover, placebo- and moxifloxacin-controlled study to assess the effects of neratinib (HKI-272) on cardiac repolarization in healthy adult subjects," Clin. Cancer Res. 16(15):4016-4023 (2010) (Epub Jul. 20, 2010).
Hung and Lau, "Basic Science of HER-2/neu: a review," Semin. Oncol. 26(4 Suppl 12):51-59 (1999).
Hynes and Lane, "ERBB Receptors and Cancer: the Complexity of Targeted Inhibitors," Nat. Rev. Cancer 5(5):341-354 (2005).
ICH Expert Working Group: "Impurities in New Drug Substances Q3A (R2), International Conference on Harmonisation of Technical Requirements for Registration of Pharmaceuticals for Human Use" (Online) 2006.
Ikediobi, "Somatic Pharmacogenomics in Cancer," Pharmacogenomics J. 8(5):305-314 (2008) (Epub Aug. 5, 2008).
International Perliminary Report on Patentability Chapter 1 for International Application No. PCT/US2009/047643 dated Dec. 18, 2010.
International Search Report for International Application No. PCT/US2008/080130, mailed Apr. 5, 2009.
International Search Report for International Patent Application No. PCT/US2009/047643, mailed Jan. 28, 2010.
Isakoff and Baselga, "Trastuzumab-DM1: building a chemotherapy-free road in the treatment of human epidermal growth factor receptor 2-positive breast cancer," J. Clin. Oncol. 29(4):351-354 (2011) (Epub Dec. 20, 2010).
Ito et al., "A Phase 1 Study of Neratinib (HKI-272) in Combination with Paclitaxel in Japanese Patients with Solid Tumors," Ann. Oncol. 21 (Suppl 8):viii103 Abstr. 298P (2010).
Ito et al., "Tolerability and safety of oral neratinib (HKI-272) in Japanese patients with advanced solid tumors," J. Clin. Oncol. 27:(suppl; abstr. e14505) (2009).
Jackisch, "Challenges in the treatment of ErbB2 (HER2)-positive breast cancer," EJC Suppl. 6(5):7-14 (2008).
Jänne et al., "Phase I dose-escalation study of the pan-HER inhibitor, PF299804, in patients with advanced malignant solid tumors," Clin. Cancer Res. 17(5):1131-1139 (2011) (Epub Jan. 10, 2011).
Jänne, "Challenges of detecting EGFR T790M in gefitinib/erlotinib-resistant tumours," Lung Cancer 60 Suppl 2:S3-S9 (2008).
Ji et al., "Epidermal growth factor receptor variant III mutations in lung tumorigenesis and sensitivity to tyrosine kinase inhibitors," Proc. Natl. Acad. Sci. U.S.A. 103(20):7817-7822 (2006) (Epub May 3, 2006).
Ji et al., "The impact of human EGFR kinase domain mutations on lung tumorigenesis and in vivo sensitivity to EGFR-targeted therapies," Cancer Cell. 9(6):485-495 (2006) (Epub May 25, 2006).
Jimeno and Hidalgo, "Pharmacogenomics of epidermal growth factor receptor (EGFR) tyrosine kinase inhibitors," Biochim. Biophys. Acta 1766(2):217-229 (2006) (Epub Sep. 12, 2006).
Johnson et al., "Impact of EGFR mutations on treatment of non-small cell lung cancer," Cancer Chemother. Pharmacol. 58(Suppl11): s5-s9 (2006).
Johnson et al., "Strategies for discovering and derisking covalent, irreversible enzyme inhibitors," Future Med. Chem. 2(6):949-964 (2010).

Johnson, "Biomarkers of Lung Cancer Response to EGFR-TKI," EJC Suppl. 5(8):14-15 Abstr. S23 (2007).
Johnson, "Protein kinase inhibitors: contributions from structure to clinical compounds," Q. Rev. Biophys. 42(1):1-40 (2009) (Epub Mar. 19, 2009).
Jones and Buzdar, "Evolving Novel Anti-HER2 Strategies," Lancet Oncol. 10(12):1179-1187 (2009).
Jones, "Adaptive trials receive boost," Nat. Rev. Drug Discov. 9(5):345-348 (2010) (Epub Apr. 23, 2010).
Jones, "HER4 intracellular domain (4ICD) activity in the developing mammary gland and breast cancer," J. Mammary Gland Biol. Neoplasia 13(2):247-258 (2008) (Epub May 13, 2008).
Jorissen et al., "Epidermal growth factor receptor: mechanisms of activation and signalling," Exp. Cell. Res. 284(1):31-53 (2003).
Joshi and Kucherlapati, "Pharmacogenomics of lung cancer: with a view to address EGFR-targeted therapies," Pharmacogenomics 8(9):1211-1220 (2007).
Kamath and Buolamwini, "Targeting EGFR and HER-2 receptor tyrosine kinases for cancer drug discovery and development," Med. Res. Rev. 26(5):569-594 (2006).
Kane, "Cancer Therapies Targeted to the Epidermal Growth Factor Receptor and Its Family Members," Expert Opin. Ther. Pat. 16(2):147-164 (2006).
Katzel et al., "Recent advances of novel targeted therapy in non-small cell lung cancer," .J Hematol. Oncool. 2:2 (2009).
Kennedy et al., "Novel Agents in the Management of Lung Cancer," Curr. Med. Chem. 17(35):42914325 (2010).
Kim et al., "Chasing targets for EGFR tyrosine kinase inhibitors in non-small-cell lung cancer: Asian perspectives," Expert Rev. Mol. Diagn.7(6):821-836 (2007).
Kim et al., "The role of HER-2 oncoprotein in drug-sensitivity in breast cancer (Review)," Oncol. Rep. 9(1):3-9 (2002).
Klein and Levitzki, "Targeting the EGFR and the PKB Pathway in Cancer," Curr. Opin. Cell. Biol. 21(2):185-193 (2009) (Epub Feb. 11, 2009).
Klüter et al., "Characterization of irreversible kinase inhibitors by directly detecting covalent bond formation: a tool for dissecting kinase drug resistance," ChemBioChem 11(18):2557-2566 (2010).
Kotteas et al., "Targeted therapy for nonsmall cell lung cancer: focusing on angiogenesis, the epidermal growth factor receptor and multikinase inhibitors," Anticancer Drugs 21(2):151-168 (2010).
Krop, "Managing Trastuzumab-resistant Breast Cancer," Clin. Adv. Hematol. Oncol. 7(2):108-110 (2009).
Kuznar, "New Small Molecule Added to Trastuzumab Improves Survival in Metastatic Disease," Am. Health Drug Benefits 2(5):27 (2009).
Kwak et al., "Irreversible inhibitors of the EGF receptor may circumvent acquired resistance to gefitinib," Proc. Natl. Acad. Sci. U.S.A. 102(21):7665-7670 (2005) (Epub May 16, 2005).
La Motta et al., "Computational studies of epidermal growth factor receptor: docking reliability, three-dimensional quantitative structure-activity relationship analysis, and virtual screening studies," J. Med. Chem. 52(4):964-975 (2009).
Laack et al., "Lessons learnt from gefitinib and erlotinib: Key insights into small-molecule EGFR-targeted kinase inhibitors in non-small cell lung cancer," Lung Cancer 69(3):259-264 (2010) (Epub Jun. 19, 2010).
Lam and Mok, "Targeted Therapy: An Evolving World of Lung Cancer," Respirology 16(1):13-21 (2011) (Epub Aug. 16, 2010).
Langer and Soria, "The role of anti-epidermal growth factor receptor and anti-vascular endothelial growth factor therapies in the treatment of non-small-cell lung cancer," Clin. Lung Cancer 11(2):82-90 (2010).
Leone and Dudek, "Enzyme replacement therapy for Gaucher's disease in patient treated for non-small cell lung cancer," Anticancer Res. 28(6B):3937-3939 (2008).
Levitzki and Mishani, "Tyrphostins and other tyrosine kinase inhibitors," Annu. Rev. Biochem. 75:93-109 (2006).
Li and Perez-Soler, "Skin toxicities associated with epidermal growth factor receptor inhibitors," Target. Oncol. 4(2):107-119 (2009) (Epub May 19, 2009).

(56) References Cited

OTHER PUBLICATIONS

Li et al., "BIBW2992, an irreversible EGFR/HER2 inhibitor highly effective in preclinical lung cancer models," Oncogene 27(34):4702-4711 (2008) (Epub Apr. 14, 2008).
Li et al., "Bronchial and peripheral murine lung carcinomas induced by T790M-L858R mutant EGFR respond to HKI-272 and rapamycin combination therapy," Cancer Cell 12(1):81-93 (2007).
Li et al., "PTEN, a putative protein tyrosine phosphatase gene mutated in human brain, breast, and prostate cancer," Science 275(5308):1943-1947 (1997).
Limentani et al., "Safety and Efficacy of Neratinib (HKI-272) in Combination with Vinorelbine in Patients with Solid Tumors," J. Clin. Oncol. (Meeting Abstracts) 27(15S):e14554 (2009).
Lin and Winer, "Chemotherapy agents in human epidermal growth factor receptor 2-positive breast cancer: time to step out of the limelight," J. Clin. Oncol. 29(3):251-253 (2011) (Epub Dec. 13, 2010).
Lin and Yang, "Epidermal growth factor receptor tyrosine kinase inhibitors in elderly or poor performance status patients with advanced non-small cell lung cancer," Target. Oncol. 4(1):37-44 (2009) (Epub Jan. 20, 2009).
Linardou et al., "Somatic EGFR mutations and efficacy of tyrosine kinase inhibitors in NSCLC," Nat. Rev. Clin. Oncol. 6(6):352-366 (2009).
Little, "Molecular Tests, Targets and Therapies for Cancer," EPC (DIA 43rd Annual Meeting Edition) p. 98 (2007).
Liu et al., "Targeting epidermal growth factor receptor in lung cancer: Perspective from the Asia-Pacific region," Asia-Pac. J. Clin. Oncol. 2:22-31 (2006).
Locker et al., "ASCO 2006 update of recommendations for the use of tumor markers in gastrointestinal cancer," J. Clin. Oncol. 24(33):5313-5327 (2006) (Epub Oct. 23. 2006).
Loew et al., "The epidermal growth factor receptor as a therapeutic target in glioblastoma multiforme and other malignant neoplasms," Anticancer Agents Med. Chem. 9(6):703-715 (2009).
Loke, "Drug-drug interactions—bridging the gulf between the bench and the bedside?" Br. J. Clin. Pharmacol. 71(4):485-486 (2011).
LoPiccolo et al., "Targeting the PI3K/Akt/mTOR pathway: effective combinations and clinical considerations," Drug Resist. Updat. 11(1-2):32-50 (2008) (Epub Dec. 31, 2007).
Loriot et al., "Drug insight: gastrointestinal and hepatic adverse effects of molecular-targeted agents in cancer therapy," Nat. Clin. Pract. Oncol. 5(5):268-278 (2008) (Epub Mar. 18, 2008).
Loriot et al., "Pemetrexed-induced pneumonitis: a case report," Clin. Lung Cancer 10(5):364-366 (2009).
Lorusso and Eder, "Therapeutic potential of novel selective-spectrum kinase inhibitors in oncology," Expert Opin. Investig. Drugs 17(7):1013-1028 (2008).
Lu and Ku, "Preformulation stability study of the EGFR inhibitor HKI-272 (Neratinib) and mechanism of degradation," Drug Dev. Ind. Pharm. 1-7 (2011).
Lu et al., "The PTEN/MMAC1/TEP tumor suppressor gene decreases cell growth and induces apoptosis and anoikis in breast cancer cells," Oncogene 18(50):7034-7045 (1999).
Lynch et al., "Novel Agents in the Treatment of Lung Cancer: Fourth Cambridge Conference," Clin. Cancer Res. 13(15 Suppl.):4583s-4588s (2007).
Lynch et al., "Summary statement novel agents in the treatment of lung cancer: Fifth Cambridge Conference assessing opportunities for combination therapy," J. Thorac. Oncol. 3(6 Suppl 2):S107-S112 (2008).
Lynch, "Molecular Staging of NSCLC: 2006," EJC (Suppl 4):24-25 Abstr. S55 (2006).
Ma et al., "PIK3CA as an oncogene in cervical cancer," Oncogene 19(23):2739-2744 (2000).
Macrinici and Romond, "Clinical updates on EGFR/HER targeted agents in early-stage breast cancer," Clin. Breast Cancer 10 Suppl 1:E38-E46 (2010).
Maehama et al., "A sensitive assay for phosphoinositide phosphatases," Anal. Biochem. 279(2):248-250 (2000).
Maehama et al., "PTEN and myotubularin: novel phosphoinositide phosphatases," Annu. Rev. Biochem. 70:247-279 (2001).
Maehama, "PTEN: its deregulation and tumorigenesis," Biol. Pharm. Bull. 30(9):1624-1627 (2007).
Mallon et al., "Antitumor efficacy of PKI-587, a highly potent dual PI3K/mTOR kinase inhibitor," Clin. Cancer Res. 17(10):3193-3203 (2011) (Epub Feb. 15, 2011).
Man et al., "New and established targets for the treatment of breast cancer," Adv. Breast Cancer 7(3):10-13 (2010).
Martinez-Garcia et al., "Tyrosine Kinase Inhibitors in Breast Cancer: Present Status and Perspectives," Cancer Chemother. Rev. 186-194 (2010).
Mauriz and Gonzalez-Gallego, "Antiangiogenic drugs: current knowledge and new approaches to cancer therapy," J. Pharm. Sci. 97(10):4129-4154 (2008).
Mayer, "Treatment of HER2-positive metastatic breast cancer following initial progression," Clin. Breast Cancer 9 Suppl 2:S50-S57 (2009).
McDermott et al., "Acquired resistance of non-small cell lung cancer cells to MET kinase inhibition is mediated by a switch to epidermal growth factor receptor dependency," Cancer Res. 70(4):1625-1634 (2010) (Epub Feb. 2, 2010).
McDermott et al., "High-throughput lung cancer cell line screening for genotype-correlated sensitivity to an EGFR kinase inhibitor," Methods Enzymol. 438:331-341 (2008).
McDermott et al., "Identification of genotype-correlated sensitivity to selective kinase inhibitors by using high-throughput tumor cell line profiling," Proc. Natl. Acad. Sci. U.S.A. 104(50):19936-19941 (2007) (Epub Dec. 6, 2007).
Mehta and Osipo, "Trastuzumab resistance: role for Notch signaling," ScientificWorldJournal 9:1438-1448 (2009).
Mendelsohn and Baselga, "The EGF receptor family as targets for cancer therapy," Oncogene 19(56):6550-6565 (2000).
Mendoza, "Targeted therapies in the treatment of advanced non-small-cell lung cancer: update," Klin.Onkol. 22(4):131-138 (2009).
Meng et al., "MicroRNA-21 regulates expression of the PTEN tumor suppressor gene in human hepatocellular cancer," Gastroenterology 133(2):647-658 (2007) (Epub May 21, 2007).
Metro and Cappuzzo, "New targeted therapies for non-small-cell lung cancer," Therapy 6(3):335-350 (2009).
Metzger-Filho et al., "Management of metastatic HER2-positive breast cancer progression after adjuvant trastuzumab therapy—current evidence and future trends," Expert Opin. Investig. Drugs 19 Suppl 1:S31-S39 (2010).
Metzger-Filho et al., "Molecular targeted therapy in prevalent tumors: learning from the past and future perspectives," Current Clin. Pharmacol. 5(3):166-177 (2010).
Minami et al., "The major lung cancer-derived mutants of ERBB2 are oncogenic and are associated with sensitivity to the irreversible EGFR/ERBB2 inhibitor HKI-272," Oncogene 26(34):5023-5027 (2007) (Epub Feb. 19, 2007).
Minkovsky and Berezov, "BIBW-2992, a dual receptor tyrosine kinase inhibitor for the treatment of solid tumors," Curr. Opin. Investig. Drugs 9(12):1336-1346 (2008).
Mitsudomi et al., "Biological and clinical implications of EGFR mutations in lung cancer," Int. J. Clin. Oncol. 11(3):190-198 (2006).
Moasser, "Targeting the function of the HER2 oncogene in human cancer therapeutics," Oncogene 26(46):6577-6592 (2007) (Epub May 7, 2007).
Morabito et al., "Methodological Issues of Clinical Research with EGFR Inhibitors," Curr. Cancer Ther. Rev. 3(4):292-302 (2007).
Moreno-Aspitia and Perez, "Treatment options for breast cancer resistant to anthracycline and taxane," Mayo Clin. Proc. 84(6):533-545 (2009).
Morozova et al., "System-level analysis of neuroblastoma tumor-initiating cells implicates AURKB as a novel drug target for neuroblastoma," Clin. Cancer Res. 16(18):4572-4582 (2010) (Epub Jul. 22, 2010).
Morris and Hudis, "Personalizing therapy for metastatic breast cancer," Expert Rev. Anticancer Ther. 9(9):1223-1226 (2009).
Morrow et al., "Recent advances in systemic therapy: Advances in systemic therapy for HER2-positive metastatic breast cancer," Breast Cancer Res. 11(4):207 (2009) (Epub Jul. 15, 2009).

(56) References Cited

OTHER PUBLICATIONS

Moy and Goss, "Lapatinib: current status and future directions in breast cancer," Oncologist 11(10):1047-1057 (2006).
Mukai, "Targeted therapy in breast cancer: current status and future directions," Jpn. J. Clin. Oncol. 40(8):711-716 (2010) (Epub Apr. 8, 2010).
Mukai, "Treatment strategy for HER2-positive breast cancer," Int. J. Clin. Oncol. 15(4):335-340 (2010) (Epub Jul. 15, 2010).
Mukherji and Spicer, "Second-generation epidermal growth factor tyrosine kinase inhibitors in non-small cell lung cancer," Expert Opin. Investig. Drugs 18(3):293-301 (2009).
Mullard, "2010 in Reflection," Nat. Rev. Drug Discov. 10:7-9 (2011).
Munagala et al., "Promising molecular targeted therapies in breast cancer," Indian J. Pharmacol. 43(3):236-245 (2011).
Mundhenke et al., "Significance of Tyrosine Kinase Inhibitors in the Treatment of Metastatic Breast Cancer," Breast Care (Basel) 4(6):373-378 (2009) (Epub Nov. 16, 2009).
Murphy and Fornier, "HER2-positive breast cancer: beyond trastuzumab," Oncology (Williston Park) 24(5):410-415 (2010).
Muthuswamy, "Trastuzumab resistance: all roads lead to SRC," Nat. Med. 17(4):416-418 (2011).
Nagata et al., "PTEN activation contributes to tumor inhibition by trastuzumab, and loss of PTEN predicts trastuzumab resistance in patients," Cancer Cell vol. 6(2):117-127 (2004).
Nahta and O'Regan, "Evolving strategies for overcoming resistance to HER2-directed therapy: targeting the PI3K/AKT/mTOR pathway," Clin. Breast Cancer 10 Suppl 3:S72-S78 (2010).
Natoli et al., "Tyrosine kinase inhibitors," Curr. Cancer Drug Targets 10(5):462-483 (2010).
Nguyen et al., "Acquired resistance to epidermal growth factor receptor tyrosine kinase inhibitors in non-small-cell lung cancers dependent on the epidermal growth factor receptor pathway," Clin. Lung Cancer 10(4):281-289(2009).
Nicholson et al., "EGFR and cancer prognosis," Eur. J. Cancer 37 Suppl 4:S9-S15 (2001).
Nielsen et al., "HER2-targeted therapy in breast cancer. Monoclonal antibodies and tyrosine kinase inhibitors," Cancer Treat Rev. 35(2):121-136 (2009) (Epub Nov. 12, 2008).
Nitz, "Perspectives: Other ErbB2-Targeted Therapies," Breast Care (Basel) 5(s1):25-27 (2010) (Epub Apr. 26, 2010).
O'Brien et al., "Activated phosphoinositide 3-kinase/AKT signaling confers resistance to trastuzumab but not lapatinib," Mol. Cancer Ther. 9(6):1489-1502 (2010) (Epub May 25, 2010).
Ocaña and Amir, "Irreversible pan-ErbB tyrosine kinase inhibitors and breast cancer: current status and future directions," Cancer Treat. Rev. 35(8):685-691 (2009) (Epub Sep. 4, 2009).
Ocaña and Pandiella, "Identifying breast cancer druggable oncogenic alterations: lessons learned and future targeted options," Clin. Cancer Res. 14(4):961-970 (2008).
Ocaña et al., "New Targeted Therapies in Head and Neck Cancer," Cancer Chemo. Rev. 4:35-43 (2009).
Ocaña et al., "Novel tyrosine kinase inhibitors in the treatment of cancer," Curr. Drug Targets 10(6):575-576 (2009).
Ocaña et al., "Preclinical development of molecular-targeted agents for cancer," Nat. Rev. Clin. Oncol. 8:200-209 (2011).
Oh et al., "Detection of epidermal growth factor receptor in the serum of patients with cervical carcinoma," Clin. Cancer Res. 6(12):4760-4763 (2000).
O'Hare et al., "Bcr-Abl kinase domain mutations and the unsettled problem of Bcr-AblT315I: looking into the future of controlling drug resistance in chronic myeloid leukemia," Clin. Lymphoma Myeloma 7 Suppl 3:S120-S130 (2007).
Omuro et al., "Lessons learned in the development of targeted therapy for malignant gliomas," Mol. Cancer Ther. 6(7):1909-1919 (2007).
O'Neil et al., (ed.). The Merck Index—An Encyclopedia of Chemicals, Drugs, and Biologicals. 13th Edition, Whitehouse Station, NJ: Merck and Co., Inc., 2001., p. 1454-1455.
Pal et al., "Targeted therapies for non-small cell lung cancer: an evolving landscape," Mol. Cancer Ther. 9(7):1931-1944 (2010) (Epub Jun. 22, 2010).
Pallis et al., "Targeted therapies in the treatment of advanced/metastatic NSCLC," Eur. J. Cancer 45(14):2473-2487 (2009).
Pantuck et al., "Prognostic relevance of the mTOR pathway in renal cell carcinoma: implications for molecular patient selection for targeted therapy," Cancer 109(11):2257-2267 (2007).
Pao and Chmielecki, "Rational, biologically based treatment of EGFR-mutant non-small-cell lung cancer," Nat. Rev. Cancer 10(11):760-774 (2010) (Epub 2010 Oct. 22, 2010).
Pao, "Defining clinically relevant molecular subsets of lung cancer," Cancer Chemother. Pharmacol. 58(Suppl 1):s11-s15 (2006).
Paridaens et al., "Neratinib (HKI-272), an irreversible pan-ErbB receptor tyrosine kinase inhibitor: Phase 2 results in patients with ErbB2+ advanced breast cancer," Ann. Oncol. 20(Suppl 2):ii61-ii62 Abstr. 186P (2009).
Pegram et al., "Expert roundtable: emerging questions in ErbB2-positive breast cancer; Feb. 22, 2007," Clin. Breast Cancer 8(Suppl 3):S131-S141 (2008).
Pegram et al., "The molecular and cellular biology of HER2/neu gene amplification/overexpression and the clinical development of herceptin (trastuzumab) therapy for breast cancer," Cancer Treat. Res. 103:57-75 (2000).
Pérez-Soler, "Individualized therapy in non-small-cell lung cancer: future versus current clinical practice," Oncogene 28(Suppl 1):S38-S45 (2009).
Pérez-Tenorio et al., "PIK3CA mutations and PTEN loss correlate with similar prognostic factors and are not mutually exclusive in breast cancer," Clin. Cancer Res. 13(12):3577-3584 (2007).
Perren et al , "Immunohistochemical evidence of loss of PTEN expression in primary ductal adenocarcinomas of the breast," Am. J. Pathol. 155(4):1253-1260 (1999).
Petter et al., "A novel small-molecule drug platform to silence cancer targets—application to the panErbB kinases," In: Proceedings of the 100th Annual Meeting of the American Association for Cancer Research; Apr. 18-22, 2009; Denver, CO. Abstr. 3746 (2009).
Piccart et al., "Beyond trastuzumab: new anti-HER2 agents," Breast 20(Suppl 1):S1-52 Abstr. S02 (2011).
Piccart, "Circumventing de novo and acquired resistance to trastuzumab: new hope for the care of ErbB2-positive breast cancer," Clin. Breast Cancer 8(Suppl 3):S100-S113 (2008).
Plati et al., "Dysregulation of apoptotic signaling in cancer: molecular mechanisms and therapeutic opportunities," J. Cell. Biochem. 104(4):1124-1149 (2008).
Plosker and Keam, "Trastuzumab: a review of its use in the management of HER2-positive metastatic and early-stage breast cancer," Drugs 66(4):449-475 (2006).
Ponz-Sarviséet al., "Epidermal growth factor receptor inhibitors in colorectal cancer treatment: what's new?" World J. Gastroenterol. 13(44):5877-5887 (2007).
Potashman and Duggan, "Covalent modifiers: an orthogonal approach to drug design," J. Med. Chem. 52(5):1231-1246 (2009).
Rabindran, "Antitumor activity of HER-2 inhibitors," Cancer Lett. 227(1):9-23 (2005) (Epub Dec. 15, 2004).
Rampaul et al., "Clinical value of epidermal growth factor receptor expression in primary breast cancer," Adv. Anat. Pathol. 12(5):271-273 (2005).
Rana and Swaby, "Targeted Therapies for HER2 Breast Cancer: A View of the Landscape," Curr. Breast Cancer Rep. 3:55-62 (2011).
Ranganathan and Muneer, "Highlights from: The 24th Annual Meeting of the American Association for Cancer Research; Los Angeles, CA; Apr. 14-18, 2007," Clin. Lung Cancer 8(6):359-363 (2007).
Ray et al., "Lung cancer therapeutics that target signaling pathways: an update," Expert Rev. Respir. Med. 4(5):631-645 (2010).
Ray et al., "The role of EGFR inhibition in the treatment of non-small cell lung cancer," Oncologist 14(11):1116-1130 (2009) (Epub Nov. 5, 2009).
Redon et al., "A simple specific pattern of chromosomal aberrations at early stages of head and neck squamous cell carcinomas: PIK3CA but not p63 gene as a likely target of 3q26-qter gains," Cancer Res. 61(10):4122-4129 (2001).

(56) References Cited

OTHER PUBLICATIONS

Rewcastle et al., "Synthesis of 4-(phenylamino)pyrimidine derivatives as ATP-competitive protein kinase inhibitors with potential for cancer chemotherapy," Curr. Org. Chem. 4(7):679-706 (2000).
Rexer et al., "Overcoming resistance to tyrosine kinase inhibitors: lessons learned from cancer cells treated with EGFR antagonists," Cell Cycle 8(1):18-22 (2009) (Epub Jan. 30, 2009).
Riely et al., "Update on epidermal growth factor receptor mutations in non-small cell lung cancer," Clin. Cancer Res. 12(24):7232-7241 (2006).
Riely, "Second-generation epidermal growth factor receptor tyrosine kinase inhibitors in non-small cell lung cancer," J. Thorac. Oncol. 3(6 Suppl 2):S146-S149 (2008).
Rosell et al., "Age-related genetic abnormalities: the Achilles' heel for customizing therapy in elderly lung cancer patients," Personalized Medicine 4(1):59-72 (2007).
Rosell et al., "Screening for epidermal growth factor receptor mutations in lung cancer," N. Engl. J. Med. 361(10):958-967 (2009) (Epub Aug. 19, 2009).
Rosell et al., "Treatment of non-small-cell lung cancer and pharmacogenomics: where we are and where we are going," Curr. Opin. Oncol. 18(2):135-143 (2006).
Rosen et al., "Targeting signal transduction pathways in metastatic breast cancer: a comprehensive review," Oncologist 15(3):216-235 (2010) (Epub Mar. 3, 2010).
Rotella, "Medicinal Chemistry—XXth International Symposium. Lead finding strategies and kinase selectivity," IDrugs 11(11):774-778 (2008).
Roukos, "Trastuzumab and beyond: sequencing cancer genomes and predicting molecular networks," Pharmacogenomics J. 11(2):81-92 (2011) (Epub Oct. 26, 2010).
Roy and Perez, "Beyond trastuzumab: small molecule tyrosine kinase inhibitors in HER-2-positive breast cancer," Oncologist 14(11):1061-1069 (2009) (Epub Nov. 3, 2009).
Rubin et al., "10q23.3 loss of heterozygosity is higher in lymph node-positive (pT2-3,N+) versus lymph node-negative (pT2-3,N0) prostate cancer," Hum. Pathol. 31(4):504-508 (2000).
Rudloff and Samuels, "A growing family: adding mutated Erbb4 as a novel cancer target," Cell Cycle. 9(8):1487-1503 (2010) (Epub Apr. 15, 2010).
Saal et al., "PIK3CA mutations correlate with hormone receptors, node metastasis, and ERBB2, and are mutually exclusive with PTEN loss in human breast carcinoma," Cancer Res. 65(7):2554-2559 (2005).
Salvesen et al., "Integrated genomic profiling of endometrial carcinoma associates aggressive tumors with indicators of PI3 kinase activation," Proc. Natl. Acad. Sci. U.S.A. 106(12):4834-4839 (2009) (Epub Mar. 4, 2009).
Samuels and Ericson, "Oncogenic PI3K and its role in cancer," Curr. Opin. Oncol. 18(1):77-82 (2006).
Sanchez-Martin and Pandiella, "Differential action of ErbB kinase inhibitors on receptor oligomerization," EJC Suppl. 8:107 Abstr. 337 (2010).
Santarpia et al., "Tyrosine kinase inhibitors for non-small-cell lung cancer: finding patients who will be responsive," Expert Rev. Respir. Med. (3):413-424 (2011).
Sartore-Bianchi et al., "Rationale and clinical results of multi-target treatments in oncology," Int. J. Biol. Markers 22(1 Suppl 4):S77-S87 (2007).
Sathornsumetee et al., "Malignant glioma drug discovery—targeting protein kinases," Expert Opin. Drug Discov. 2(1):1-17 (2007).
Sattler et al., "EGFR-targeted therapeutics: focus on SCCHN and NSCLC," ScientificWorldJournal 8:909-919 (2008).
Saura et al., "Safety of Neratinib (HKI-272) in Combination with Capecitabine in Patients with Solid Tumors: A Phase 1/2 Study," Cancer Res. 69(24 Suppl) Abstr. 5108 (2009).
Saura et al., "The safety of Neratinib (HKI-272) in Combination with Capecitabine in Patients with Solid Tumors: A Phase 1/2 Study," Ann. Oncol. 21(Suppl 4):iv63 Abstr. 147P (2010).

Saura et al., (Dec. 2011). Safety and Efficacy of Neratinib in Combination with Capecitabine in Patients with ErbB2-Positive Breast Cancer. Poster presented at the 2011 CTRC-AACR San Antonio Breast Cancer Symposium, San Antonio, Texas.
Schiller et al., "Comparison of four chemotherapy regimens for advanced non-small-cell lung cancer," N. Engl. J. Med. 346(2):92-98 (2002).
Scott and Salgia, "Biomarkers in lung cancer: from early detection to novel therapeutics and decision making," Biomark. Med. 2(6):577-586 (2008).
Sebastian et al., "The complexity of targeting EGFR signalling in cancer: from expression to turnover," Biochim. Biophys. Acta. 1766(1):120-139 (2006) (Epub Jun. 23, 2006).
Sequist and Dziadziuszko, "Update on epidermal growth factor receptor inhibitor development in lung cancer," J. Thorac. Oncol. 1(7):740-743 (2006).
Sequist et al., "Neratinib, an irreversible pan-ErbB receptor tyrosine kinase inhibitor: results of a phase II trial in patients with advanced non-small-cell lung cancer," J. Clin. Oncol. 28(18):3076-3083 (2010) (Epub May 17, 2010).
Sequist, "Second-generation epidermal growth factor receptor tyrosine kinase inhibitors in non-small cell lung cancer," Oncologist 12(3):325-330 (2007).
Settleman and Kurie, "Drugging the bad "AKT-TOR" to overcome TKI-resistant lung cancer," Cancer Cell 12(1):6-8 (2007).
Seyhan et al., "A genome-wide RNAi screen identifies novel targets of neratinib sensitivity leading to neratinib and paclitaxel combination drug treatments," Mol. Biosyst. 7(6):1974-1989 (2011) (Epub Apr. 12, 2011).
Sharma and Jayanth, "Neratinib, an irreversible erbB receptor tyrosine Kinase inhibitor, in patients with advanced erbB2-positive breast cancer," [commentary] Adv. Breast Cancer 7(1):21 (2010).
Sharma and Settleman, "Oncogene addiction: setting the stage for molecularly targeted cancer therapy," Genes Dev. 21(24):3214-3231 (2007).
Sharma et al., "Epidermal growth factor receptor mutations in lung cancer," Nat. Rev. Cancer7(3):169-181 (2007).
Sharma et al., "Receptor tyrosine kinase inhibitors as potent weapons in war against cancers," Curr. Pharm. Des. 15(7):758-776 (2009).
Shayesteh et al., "PIK3CA is implicated as an oncogene in ovarian cancer," Nat. Genet. 21(1):99-102 (1999).
Shimamura and Shapiro, "Heat shock protein 90 inhibition in lung cancer," J. Thorac. Oncol. 3(6 Suppl 2):S152-S159 (2008).
Shimamura et al., "Hsp90 inhibition suppresses mutant EGFR-T790M signaling and overcomes kinase inhibitor resistance," Cancer Res. 68(14):5827-5838 (2008).
Shimamura et al., "on-small-cell lung cancer and Ba/F3 transformed cells harboring the ERBB2 G776insV_G/C mutation are sensitive to the dual-specific epidermal growth factor receptor and ERBB2 inhibitor HKI-272," Cancer Res. 66(13):6487-6491 (2006).
Sibilia et al., "The epidermal growth factor receptor: from development to tumorigenesis," Differentiation 75(9):770-787 (2007).
Sigal, "Basic science for the clinician 48: tyrosine kinases in disease: the potential for inhibitors in the treatment of immunologic diseases," J. Clin. Rheumatol. 14(1):45-48 (2008).
Simon et al., "By 1023/SK&F 96022: biochemistry of a novel (H+ + K+)-ATPase inhibitor," Biochem Pharmacol. 39(11):1799-1806 (1990).
Singh et al., "Targeted covalent drugs of the kinase family," Curr. Opin. Chem. Biol. 14(4):475-480 (2010) (Epub Jul. 6, 2010).
Singh et al., "The resurgence of covalent drugs," Nat. Rev. Drug Discov. 10(4):307-317 (2011).
Smith, "Goals of Treatment of Patients with Metastatic Breast Cancer," Semin. Oncol. 33:S2-S5 (2006).
Solca et al., "Beyond Trastuzumab: Second-Generation Targeted Therapies for HER-2-Positive Breast Cancer," Drugs for HER-2-positive Breast Cancer, Milestones in Drug Therapy, 2011 p. 91-107 (2011).
Specht and Gralow, "Neoadjuvant chemotherapy for locally advanced breast cancer," Semin. Radiat. Oncol. 9(4):222-228 (2009).
Spector et al., "Small Molecule HER-2 Tyrosine Kinase Inhibitors," Breast Cancer Res. 9(2):205 (2007).

(56) References Cited

OTHER PUBLICATIONS

Spector, "Treatment of metastatic ErbB2-positive breast cancer: options after progression on trastuzumab," Clin. Breast Cancer 8 Suppl 3:S94-S99 (2008).
Spicer and Rudman, "EGFR inhibitors in non-small cell lung cancer (NSCLC): the emerging role of the dual irreversible EGFR/HER2 inhibitor BIBW 2992," Target Oncol. 5(4):245-255 (2010) (Epub Jun. 24, 2010).
Srivastava et al., "Synthesis and structure-activity relationships of potent antitumor active quinoline and naphthyridine derivatives," Anticancer Agents Med. Chem. 7(6):685-709 (2007).
Staroslawska et al. (Dec. 2010). Safety and Efficacy of Neratinib (HKI-272) Plus Vinorelbine in the Treatment of Patients With ErbB2+ Metastatic Breast Cancer Pretreated With Anti-Her2 Therapy. Poster presented at teh 33rd Annual San Antonio Breast Cancer Symposium, San Antonio, Texas.
Stebbing et al., "Lemur tyrosine kinase-3 (LMTK3) in cancer and evolution," Oncotarget 2(6):428-429 (2011).
Steins et al., "Targeting the epidermal growth factor receptor in non-small cell lung cancer," Onkologie 33(12):704-709 (2010) (Epub Nov. 26, 2010).
Stemke-Hale et al., "An integrative genomic and proteomic analysis of PIK3CA, PTEN, and AKT mutations in breast cancer," Cancer Res. 68(15):6084-6091 (2008).
Stokoe et al., "Dual role of phosphatidylinositol-3,4,5-trisphosphate in the activation of protein kinase B," Science 277(5325):567-570 (1997).
Swaby et al., "Neratinib in combination with trastuzumab for the treatment of advanced breast cancer: A phase I/II study," J. Clin. Oncol. 27:15s(suppl; abstr 1004) (2009).
Tagliabue et al., "HER2 as a target for breast cancer therapy," Expert Opin. Biol. Ther. 10(5):711-724 (2010).
Takada, "API Form Screening and Selection in Drug Discovery Stage," Pharm Stage 6(10):20-25 (2007). [English Translation Not Available].
Tjin Tham Sjin et al., "Design of a novel covalent EGFR mutant-selective inhibitor," EJC Suppl. 8(7):31 Abstr. 73 (2010).
Toffoli et al., "Pharmacology of epidermal growth factor inhibitors," Int. J. Biol. Markers 22(1 Suppl 4):524-539 (2007).
Tolaney and Krop, "Mechanisms of trastuzumab resistance in breast cancer," Anticancer Agents Med. Chem. 9(3):348-355 (2009).
Tolaney et al., "HER2-Positive Breast Cancer," JCOM 14(7):395-403 (2007).
Tomillero and Moral, "Gateways to Clinical Trials," Methods Find. Exp. Clin. Pharmacol. 31(3):183-226 (2009).
Tomillero and Moral, "Gateways to Clinical Trials," Methods Find. Exp. Clin. Pharmacol. 31(10):661-700 (2009).
Tookman and Roylance, "New Drugs for Breast Cancer," Br. Med. Bull. 96:111-129 (2010) (Epub Sep. 23, 2010).
Torres and Harris, "Polycystic kidney disease: genes, proteins, animal models, disease mechanisms and therapeutic opportunities," J. Intern. Med. 261(1):17-31 (2007).
Traxler, "Tyrosine kinase inhibitors in cancer treatment (Part II)," Exp. Opin. Ther. Patents 8(12):1599-1625 (1998).
Tsou et al., "Optimization of 6,7-Disubstituted-4-(Arylamino)Quinoline-3-Carbonitriles as Orally Active, Irreversible Inhibitors of Human Epidermal Growth Factor Receptor-2 Kinase Activity," J. Med. Chem. 48(4):1107-1131 (2005).
Tsou, "American Chemical Society—226th National Meeting. Novel Substituted 4-Anilinoquinoline-3-carbonitriles as orally active, irreversible binding inhibitors of HER-2 Kinase," (abstr. 14) 2003.
Twelves et al., "Erlotinib in combination with capecitabine and docetaxel in patients with metastatic breast cancer: a dose-escalation study," Eur. J. Cancer 44(3):419-426 (2008) (Epub Jan. 30, 2008).
Untch, "Targeted Therapy for Early and Locally Advanced Breast Cancer," Breast Care (Basel) 5(3):144-152 (2010) (Epub Jun. 16, 2010).
Upeslacis, Janis, Meeting At McGill University, Canada, Evolution of Kinase Inhibitors At Wyeth, Oct. 16, 2002.

Van Arnum, "Evaluating late-stage pipelines and potential: will 2011 be a more promising year for new molecular entities? A review of Big Pharma's late-stage pipeline shows what might lie ahead." Pharmaceutical Technology 35.2 (2011): 52+. Expanded Academic ASAP. Web. Jul. 18, 2011.
Vasudevan et al., "AKT-independent signaling downstream of oncogenic PIK3CA mutations in human cancer," Cancer Cell 16(1):21-32 (2009).
Vazquez et al., "HER2-Positive Breast Cancer: Analysis of Efficacy in Different Groups," Cancer Chemother. Rev. 4(4):224-240 (2009).
Vivanco and Mellinghoff, "Epidermal growth factor receptor inhibitors in oncology," Curr. Opin. Oncol. 22(6):573-578 (2010).
Von Eyben, "Epidermal growth factor receptor inhibition and non-small cell lung cancer," Crit. Rev. Clin. Lab. Sci. 43(4):291-323 (2006).
Vora et al., "Novel Therapeutics in Breast Cancer—Looking to the Future," Update on Cancer Therapeutics 3:189-205 (2009).
Wagner and Kaufmann, "Prospects for the Use of ATR Inhibitors to Treat Cancer," Pharmaceuticals 3:1311-1334 (2010).
Walko and Lindley, "Capecitabine: a review," Clin. Ther. 27(1):23-44 (2005).
Wang et al., "Characterization of HKI-272 covalent binding to human serum albumin," Drug Metab. Dispos. 38(7):1083-1093 (2010) (Epub Apr. 16, 2010).
Weber, "Toward a molecular classification of cancer," Toxicology Dec. 5, 2010;278(2):195-198 (2010) (Epub Oct. 24, 2009).
Wen and Drappatz, "Novel therapies for meningiomas," Expert Rev. Neurother. 6(10):1447-1464 (2006).
Wheatley-Price and Shepherd, "Epidermal growth factor receptor inhibitors in the treatment of lung cancer: reality and hopes," Curr. Opin. Oncol. 20(2):162-175 (2008).
Whenham et al., "HER2-positive breast cancer: from trastuzumab to innovatory anti-HER2 strategies," Clin. Breast Cancer 8(1):38-49 (2008).
Widakowich et al., "Molecular targeted therapies in breast cancer: where are we now?" Int. J. Biochem. Cell. Biol. 2007;39(7-8):1375-1387 (2007) (Epub May 4, 2007).
Wissner et al., "Dual irreversible kinase inhibitors: quinazoline-based inhibitors incorporating two independent reactive centers with each targeting different cysteine residues in the kinase domains of EGFR and VEGFR-2," Bioorg. Med. Chem. 15(11):3635-4368 (2007) (Epub Mar. 23, 2007).
Woenckhaus et al., "Prognostic value of PIK3CA and phosphorylated AKT expression in ovarian cancer," Virchows Arch. 450(4):387-395 (2007) (Epub Feb. 15, 2007).
Wondrak, "Redox-directed cancer therapeutics: molecular mechanisms and opportunities," Antioxid. Redox Signal. 11(12):3013-3069 (2009).
Wong et al., "HKI-272, an irreversible pan ErbB receptor tyrosine kinase inhibitory: Preliminary phase 1 results in patients with solid tumors," J. Clin. Oncol. 24(18S):125s Abstr. 3018 (2006).
Wong, "HKI-272 in non small cell lung cancer," Clin. Cancer Res. 13(15 Pt 2):4593s-4596s (2007).
Wong, "Searching for a magic bullet in NSCLC: the role of epidermal growth factor receptor mutations and tyrosine kinase inhibitors," Lung Cancer 60(Suppl 2):S10-S18 (2008).
Written Opinion of the International Searching Authority for International Application No. PCT/US2009/047643 dated Dec. 17, 2010.
Wu et al., "Design and synthesis of tetrahydropyridothieno[2,3-d]pyrimidine scaffold based epidermal growth factor receptor (EGFR) kinase inhibitors: the role of side chain chirality and Michael acceptor group for maximal potency," J. Med. Chem. 53(20):7316-7326 (2010).
Wu et al., "Somatic mutation and gain of copy number of PIK3CA in human breast cancer," Breast Cancer Res. 7(5):R609-R616 (2005) (Epub May 31, 2005).
Wu et al., "TAK-285, a Novel HER2/EGFR Inhibitor, Penetrates the CNS in Rats with an Intact Blood Brain Barrier (BBB),"Cancer Res. 69(24 Suppl): Abstr. 5098 (2009).
Wu et al., "Uncommon mutation, but common amplifications, of the PIK3CA gene in thyroid tumors," J. Clin. Endocrinol. Metab. 90(8):4688-4693 (2005) (Epub May 31, 2005).

(56) References Cited

OTHER PUBLICATIONS

Wykosky et al., "Therapeutic targeting of epidermal growth factor receptor in human cancer: successes and limitations," Chin. J. Cancer 30(1):5-12 (2011).

Xu et al., "Acquired resistance of lung adenocarcinoma to EGFR-tyrosine kinase inhibitors gefitinib and erlotinib," Cancer Biol. Ther. 9(8):572-582 (2010) (Epub Apr. 26, 2010).

Yoshida et al., "Targeting epidermal growth factor receptor: central signaling kinase in lung cancer," Biochem. Pharmacol. 80(5):613-623 (2010) (Epub May 24, 2010).

Yuan and Cantley, "PI3K pathway alterations in cancer: variations on a theme," Oncogene 27(41):5497-5510 (2008).

Yun et al., "The T790M mutation in EGFR kinase causes drug resistance by increasing the affinity for ATP," Proc. Natl. Acad. Sci. U.S.A. 105(6):2070-2075 (2008) (Epub Jan. 28, 2008).

Yuza et al., "Allele-dependent variation in the relative cellular potency of distinct EGFR inhibitors," Cancer Biol. Ther. 6(5):661-667 (2007) (Epub Feb. 13, 2007).

Zaczek et al., "The diverse signaling network of EGFR, HER2, HER3 and HER4 tyrosine kinase receptors and the consequences for therapeutic approaches," Histol. Histopathol. 20(3):1005-1015 (2005).

Zahnow, "ErbB receptors and their ligands in the breast," Expert Rev. Mol. Med. 8(23):1-21 (2006).

Zhang et al. Xenograft Models of Breast Cancer: the Link between Characteristics of Biomarker Expression and the Anti-tumor Effect of the Representative Therapies [abstract]. In: Proceedings of the 101st Annual Meeting of the American Association for Cancer Research; Apr. 17-21, 2010; Washington, DC. Philadelphia (PA): AACR; Cancer Res 2010;70(8 Suppl):Abstract nr 647.

Zhang et al., "Advances in preclinical small molecules for the treatment of NSCLC," Expert Opin. Ther. Pat. 19(6):731-751 (2009).

Zhao et al., "Neratinib Reverses ATP-Binding Cassette Bl-Mediaed Chemotherapeutic Drug Resistance in Vitro, in Vivo, and Ex-Vivo," Mol. Pharmacal. 82: 47-58 (2012).

Zhou et al., "Activation of the PTEN/Mtor/STAT3 Pathway in Breast Cancer Stem-Like Cells is Required for Viability and Maintenance," Proc. Natl. Acad. Sci. U.S.A. 104:16158-16163 (2007).

Zhou et al., "Novel Mutant-Selective EGFR Kinase Inhibitors Against EGFR T790M," Nature 462(7276):1070-1074 (2009).

Genentech, Herceptino®-Product Literature, www.Genetech.com, Sep. 1998 Revised (Jun. 2014), pp. 1-35.

\* cited by examiner

TREATMENT REGIMEN UTILIZING NERATINIB FOR BREAST CANCER

This application is a 371 application of PCT/US2010/028448, filed on Mar. 24, 2010, which claims the benefit of U.S. Provisional Application No. 61/166,796 filed on Apr. 6, 2009, the contents of which is hereby incorporated by reference in its entirety.

BACKGROUND OF THE INVENTION

Breast cancer is the most frequently diagnosed malignancy in women and the leading cause of cancer mortality in women worldwide. The global incidence of breast cancer is estimated to reach 5 million women in the next decade [Parkin, D M and Fernandez L M, Use of statistics to assess the global burden of breast cancer. *Breast Journal.* 2006; (12, Suppl 1):S70-80; World Health Statistics. 2008, World Health Organization.] In 2007, breast cancer accounted for approximately 540,000 deaths worldwide [World Health Organization Fact Sheet No. 297. 2008; available from WHO web site.]

The erbB (erythroblastic leukemia viral oncogene homolog) family of TKIs (Tyrosine Kinase Inhibitors) consists of 4 members: erbB-1 (EGFR [epidermal growth factor receptor]), erbB-2 (HER-2, neu), erbB-3 (HER-3) and erbB-4 (HER-4). The erbB family of receptors is involved in cell proliferation, tumorigenesis, and metastasis and is abnormally expressed in multiple tumor types. HER2-positive breast cancers, i.e., those which test positive for the protein called human EGFR, are associated with Erb-2-protein overexpression or erbB-2 gene amplification in breast cancer tumors has been associated with more aggressive clinical disease and poorer prognosis [Slamon D, Human breast cancer: correlation of relapse and survival with amplification of the HER-2/neu oncogene. *Science.* 1987 (235):177-182].

Trastuzumab, a humanized monoclonal antibody that selectively binds to the human erbB-2 receptor, improves the prognosis of women with erbB-2-positive breast cancer. In patients with erbB-2 overexpressing metastatic breast cancer, trastuzumab in combination with chemotherapy improves tumor regression, extends time to tumor progression and prolongs median survival over chemotherapy alone resulting in its approval as first-line treatment in the metastatic setting. [Ligibel J A and Winer E P, Trastuzumab/chemotherapy combinations in metastatic breast cancer. *Seminars in Oncology.* 2002; 29(3 Suppl 11): 38-43]. Herceptin (trastuzumab) [Package insert, Genentech (2008)]. Trastuzumab has also been approved for use in the adjuvant setting in combination with other drugs for treatment of erbB-2 overexpressing node positive or node negative (estrogen receptor/progesterone receptor [ER/PgR] negative) metastatic breast cancer. Thus, trastuzumab has been used as part of a treatment regimen consisting of (a) doxorubicin, cyclophosphamide, and either paclitaxel or docetaxel, (b) a regimen with docetaxel and carboplatin, and (c) as a single agent following multi-modality anthracycline based therapy.

The current standard of care after diagnosis with HER+ breast cancer is surgery, followed by adjuvant treatment for a year. Standard adjuvant treatment is some combination of chemotherapy, radiation, hormonal therapy for ER/PR positive disease and trastuzumab. Despite completion of adjuvant therapy, patients with early stage breast cancer remain at risk for relapse. Published reports of trastuzumab therapy show disease-free-survival rates ranging from 80.6% [Smith I, et al. 2-year follow-up of trastuzumab after adjuvant chemotherapy in HER2-positive breast cancer: a randomized controlled trial. *Lancet.* 2007; 369:29-36] at three years to 85.9% to 82% at four years [Perez E A, et al., Updated results of the combined analysis of NCCTG N9831 and NSABP B-31 adjuvant chemotherapy with/without trastuzumab in patients with HER2-positive breast cancer. *Journal of Clinical Oncology.* ASCO Annual Meeting Proceedings. 2007; 25(18S): 512 and Slamon D, et al., Phase III trial comparing AC-T with AC-TH and with TCH in the adjuvant treatment of HER2 positive early breast cancer patients: second interim efficacy analysis. Presentation by Slamon D. SABCC 2006].

HKI-272 (neratinib) has been described for the treatment of neoplasms [U.S. Pat. No. 6,288,082]. Neratinib is a potent irreversible pan erbB inhibitor. Neratinib is an orally available small molecule that inhibits erbB-1, erbB-2 and erbB-4 at the intracellular tyrosine kinase domains, a mechanism of action that is different from trastuzumab. Neratinib reduces erbB-1 and erbB-2 autophosphorylation, downstream signaling, and the growth of erbB-1 and erbB-2 dependent cell lines. Preclinical data suggest that neratinib will have antitumor activity in erbB-1- and/or erbB 2-expressing carcinoma cell lines, with cellular IC50<100 nM [Rabindran S K, et al. Antitumor activity of HKI-272, an orally active, irreversible inhibitor of the HER-2 tyrosine kinase. *Cancer Research.* 2004; 64(11):3958-65].

What are needed are drugs and regimens which improve patient survival rates and/or drugs and regimens which decrease recurrence of breast cancer following completion of primary and adjuvant treatment.

SUMMARY OF THE INVENTION

In one aspect, the invention provides a regimen for treatment of a HER-2/neu overexpressed/amplified neoplasm comprising delivering a course of neratinib therapy as an extension of trastuzumab adjuvant therapy, to HER-2/neu overexpressed/amplified cancer patients, e.g., neratinib is delivered following the completion of surgery and standard adjuvant therapy.

In another aspect, the invention provides a method or regimen for decreasing rate of recurrence of HER-2/neu overexpressed/amplified breast cancer in patients as compared to patients receiving only primary and trastuzumab adjuvant therapy. The method involves delivering neratinib to said patients following primary therapy and standard adjuvant therapy with trastuzumab. In one embodiment, the method also follows completion of one or more conventional neoadjuvant or standard adjuvant therapies.

In still another aspect, the invention provides a regimen for improving invasive disease free survival comprising treating cancer patients with neratinib following completion of primary and standard adjuvant therapy with trastuzumab. In one embodiment, the treatment with neratinib commences within two weeks to forty-eight months following post-surgical and standard adjuvant therapy with trastuzumab.

Still other aspects and advantages of the invention will be readily apparent from the following detailed description of the invention.

DETAILED DESCRIPTION OF THE INVENTION

In one embodiment, the invention provides an extended adjuvant regimen for treatment of HER-2/neu overexpressed/amplified cancer comprising delivering a course of neratinib therapy to HER-2/neu overexpressed/amplified cancer patients. Such extended adjuvant therapy involves beginning the neratinib therapy at the completion of adjuvant therapy with trastuzumab. This extended adjuvant therapy is used to provide improved invasive disease-free survival (IDFS) or disease-free survival (DFS)-ductal carcinoma in situ (DCIS) and/or improvements in overall survival, time to distant recurrence, and/ distant disease-free survival.

As used herein, invasive disease-free survival (IDFS) is defined as time from date of randomization to date of an IDFS event, including: invasive ipsilateral breast tumor recurrence, local/regional invasive recurrence, distant recurrence, death from any cause, invasive contralateral breast cancer, and second primary invasive cancer (nonbreast). DFS-DCIS is defined as the time from randomization to the first occurrence of any IDFS event or ductal carcinoma in situ. Distant Disease Free Survival (DDFS) is the time from randomization to the first distant recurrence, or death from any cause. Time to distant recurrence (TTDR) is defined as the time between randomization and the date of the first distant tumor recurrence, ignoring locoregional recurrences and second breast or nonbreast cancers and taking into account deaths before recurrence of distant breast cancer as censoring events.

Thus, the extended adjuvant therapy of the invention using neratinib increases the disease-free survival by reducing the risk of recurrence or death. In one embodiment, the extended neratinib adjuvant therapy reduces the risk, i.e., hazard rate, of cancer recurrence or death by 30% or 20% compared to conventional observation after trastuzumab therapy.

In another embodiment, using the extended neratinib regimen described herein, less than 15%, less than 10% and/or less than 5% of patients who have received primary and adjuvant therapy have cancer at three years post-inception of therapy. In still another embodiment, using the extended neratinib regimen described herein, less than 20%, less than 15% and/or less than 5% of patients who have received primary and adjuvant therapy have cancer at five years post inception of therapy.

As used herein, neratinib refers to HKI-272, which has the following core structure:

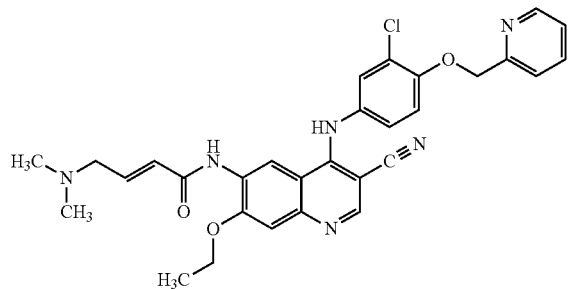 [SMILES: CCOc1cc2ncc(C#N)c(Nc3ccc(OCc4ccccn4)c(Cl)c3)c2cc1NC(=O)/C=C/CN(C)C]

in its free base form. Optionally, a pharmaceutically acceptable salt or hydrate thereof may be used. The core structure represented above is a particular HKI-272 compound, called HKI-272 or neratinib, which has the chemical name [(2E)-N-[4-[[3-chloro-4-[(pyridin-2-yl)methoxy]phenyl]amino]-3-cyano-7-ethoxyquinolin-6-yl]- 4-(dimethylamino)but-2-enamide].

Although currently less preferred, another HKI-272 compound may be used in the place of neratinib. "A HKI-272 compound" refers, in one embodiment, to a compound derived from the core structure of neratinib shown above. Suitable derivatives may include, e.g., an ester, ether, or carbamate. Such an HKI-272 compound may have the structure:

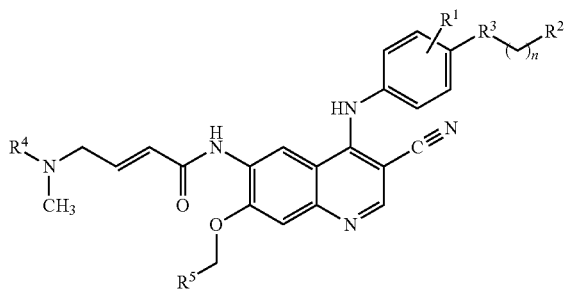

wherein:
$R^1$ is halogen;
$R^2$ is pyridinyl, thiophenyl, pyrimidinyl, thiazolyl, or phenyl, wherein $R^2$ is optionally substituted with up to three substituents;
$R^3$ is O or S;
$R^4$ is $CH_3$ or $CH_2CH_2OCH_3$;
$R^5$ is $CH_3$ or $CH_2CH_3$; and
n is 0 or 1.

The term "halogen" as used herein refers to Cl, Br, I, and F.

Also encompassed are pharmaceutically acceptable salts, hydrates, and prodrugs of neratinib and/or the other HKI compounds described herein. "Pharmaceutically acceptable salts and esters" refers to salts and esters that are pharmaceutically acceptable and have the desired pharmacological properties. Such salts include, e.g., salts that can be formed where acidic protons present in the compounds are capable of reacting with inorganic or organic bases. Suitable inorganic salts include, e.g., those formed with the alkali metals or alkaline earth metals, e.g. sodium, potassium, magnesium, calcium, aluminum. Suitable organic salts also include, e.g., those formed with organic bases such as the amine bases, e.g., ethanolamine, diethanolamine, triethanolamine, tromethamine, N-methylglucamine, and the like, and those which can form N-tetraalkylammonium salts such as N-tetrabutylammonium salts. Pharmaceutically acceptable salts can also include acid addition salts formed from the reaction of basic moieties, such as amines, in the parent compound with inorganic acids (e.g., hydrochloric and hydrobromic acids) and organic acids (e.g., acetic acid, citric acid, maleic acid, propionic, lactic, tartaric, succinic, fumaric, maleic, malonic, mandelic, malic, phthalic, hydrochloric, hydrobromic, phosphoric, nitric, sulfuric, and the alkane- and arene-sulfonic acids such as methanesulfonic acid and benzene-sulfonic acid naphthalenesulfonic, toluenesulfonic, camphorsulfonic). Other suitable examples of pharmaceutically acceptable salts include, but are not limited, to sulfate; citrate, acetate; oxalate; chloride; bromide; iodide; nitrate; bisulfate; phosphate; acid phosphate; isonicotinate; lactate; salicylate; acid citrate; tartrate; oleate; tannate; pantothenate; bitartrate; ascorbate; succinate; maleate; gentisinate; fumarate; gluconate; glucaronate; saccharate; formate; benzoate; glutamate; methanesulfonate; ethanesulfonate; benzene-sulfonate; p-toluenesulfonate; pamoate (i.e., 1,1'-methylene-bis-(2-hydroxy-3-naphthoate)); and salts of fatty acids such as caproate, laurate, myristate, palmitate, stearate, oleate, linoleate, and linolenate salts.

Pharmaceutically acceptable esters include esters formed from carboxy, sulfonyloxy, and phosphonoxy groups present in the compounds of the invention, e.g., straight chain alkyl esters having from 1 to 6 carbon atoms or branched chain alkyl groups containing 1 to 6 carbon atoms, including methyl, ethyl, propyl, butyl, 2-methylpropyl and 1,1-dimethylethyl esters, cycloalkyl esters, alkylaryl esters, benzyl esters, and the like. When there are two acidic groups present, a pharmaceutically acceptable salt or ester can be a mono-acid-mono-salt or ester or a di-salt or ester; and similarly where there are more than two acidic groups present, some or all of such groups can be salified or esterified. Compounds utilized herein may be present in unsalified or unesterified form, or in salified and/or esterified form, and the naming of such compounds is intended to include both the original (unsalified and unesterified) compound and its pharmaceutically acceptable salts and esters. Also, one or more compounds utilized herein may be present in more than one stereoisomeric form, and the naming of such compounds is intended to include all single stereoisomers and all mixtures (whether racemic or otherwise) of such stereoisomers.

The preparation of HKI-272 compounds, of which neratinib is a species, are described in detail in US Patent Application Publication No. 2005/0059678, which is hereby incorporated by reference. See, also, U.S. Pat. Nos. 6,288,082, U.S. Pat. No. 6,002,008, U.S. Pat. No. 6,297,258 and US Patent Application Publication No. 2007/0104721, which are hereby incorporated by reference. The methods described in these documents can also be used to prepare neratinib and/or the other HKI-272 and substituted 3-quinoline compounds used herein and are hereby incorporated by reference. In addition to the methods described in these documents, International Patent Publication Nos. WO-96/33978 and WO-96/33980, which are hereby incorporated by reference, describe methods that are useful for the preparation of these HKI-272 compounds. Although these methods describe the preparation of certain quinazolines, they are also applicable to the preparation of correspondingly substituted 3-cyanoquinolines and are hereby incorporated by reference.

The term "treating" or "treatment" refers to the administration of the neratinib to a subject to prevent or delay, to alleviate, or to arrest or inhibit development of the symptoms or conditions associated with neoplasms.

Trastuzumab, and methods of making and formulating same have been described. See, e.g., U.S. Pat. No. 6,821,515; U.S. Pat. No. 6,399,063 and U.S. Pat. No. 6,387,371. Trastuzumab is available commercially from Genentech under the name "Herceptin". As used herein, the term "a trastuzumab" includes includes trastuzumab and altered forms of, and derivatives of, trastuzumab. The term "a trastuzumab" includes agents that target the same epitope on the Her-2 receptor as targeted by trastuzumab. The epitope is known from H. S. Cho et al., Structure of the extracellular region of HER2 alone and in complex with the Herceptin Fab, *Nature* 421 (2003), pp. 756-760.

As used herein, neoplasms which amplify/overexpress erB-2 (used interchangeably with Her-2 and neu) include certain breast cancers and other neoplasms, which may include, ovarian, bladder, gastric, pancreatic, colorectal, prostate, and lung cancers, including non-small cell lung cancers. Other neoplasms in which ErbB1 is expressed or overexpressed include a variety of solid human tumors, including non-small cell lung (NSCL), prostate, breast, colorectal, and ovarian cancers. Methods for screening samples to determine if the neoplasm overexpresses erb-1 and/or erB-2/Her-2 are known to those of skill in the art.

Primary and Adjuvant Anti-Neoplastic Therapy

As defined herein, primary therapy is the initial therapy provided to a patient following diagnosis with a neoplasm, such as a HER-2/neu overexpressed/amplified neoplasm. Primary therapy is also called definitive local therapy. Primary therapy for a HER-2/neu overexpressed/amplified neoplasm includes surgery (in the case of breast cancer this may include lumpectomy, modified radical mastectomy, mastectomy) and/or radiation, alone or in combination. Adjuvant therapy refers to therapy conventionally provided following initial or primary therapy to increase the likelihood of a cure. Currently, standard adjuvant therapy for a HER-2/neu overexpressed/amplified neoplasm includes, e.g., chemotherapy and/or antibody therapy. Typically, if one or more of these adjuvant therapies is delivered prior to primary therapy (e.g., surgery), it is termed neoadjvant therapy. Throughout the following portions of the specification, the term "neo/adjuvant" is used as shorthand to refer to both neoadjuvant and standard adjuvant therapy. One or more types of adjuvant therapy may be delivered concomitantly.

In one embodiment, the patient may have been subject to chemotherapy involving delivery of either an anthracycline or a taxane or any cyclophosphamide, methotrexate and 5-fluorouracil regimen. Such chemotherapies may include one or more of an anthracycline, such as doxorubicin, cyclophosphamide, paclitaxel, docetaxel, and carboplatin. Another suitably neo/adjuvant therapy is a multi-modality anthracycline based therapy. Still other neo/adjuvant therapies include lapatinib [Lapatinib ditoxylate, TYKERB®], pertuzumab [Roche, Genentech], bevacizumab [Avastin®, Genentech], trastuzumab-DM-1 [Genentech], amongst others. The selection of the neoadjuvant or adjuvant therapy is not a limitation of the present invention. The extended adjuvant therapy of the invention begins following completion of therapy with trastuzumab. Trastuzumab is typically delivered after completion of or concurrent with chemotherapy as maintenance therapy. For trastuzumab, single doses and multiple doses are contemplated. In one embodiment, a single loading dose of trastuzumab is administered as a 90-minute intravenous infusion in a range of about 4-5 mg/kg on day 1, followed by about 2 mg/kg per week starting on day 8. Typically, 3 weeks is 1 cycle. From 1, to 2 to 3, weeks may be provided between cycles. In another embodiment, trastuzumab is delivered with an every-3-weeks dosing schedule, using 8 mg/kg as a loading dose and 6 mg/kg as the maintenance dose. Trastuzumab may also be given at a dose of 6 mg/kg once every 3-4 weeks. Still other trastuzumab dosing regimens may be designed and utilized.

In one embodiment, the patient may have received primary as well as, in addition to trastuzumab neo/adjuvant therapy, other neo/adjuvant therapy. In one embodiment, one or more of the adjuvant therapies may continue following completion of the trastuzumab therapy during the extended adjuvant therapy. Suitably, neither the primary therapy nor the neo/adjuvant therapy involves neratinib therapy prior to the onset of the extended neratinib regimen of the invention.

Extended Neratinib Regimen of Invention

In one embodiment, the extended neratinib regimen described herein is initiated at about one year, about two years or about three years following the start of primary therapy. The extended neratinib adjuvant regimen is started following the completion of neo/adjuvant therapy with trastuzumab. Completion of adjuvant therapy with The extended regimen described herein may start following completion of at least one dose, at least 3 week cycle, at least three 3 week cycles, at least four months, at least six months, at least eight months, or at least one year of trastuzumab neo/adjuvant therapy. In one embodiment, the extended neratinib regimen is initiated at least about two weeks, at least about one month, at least about six months, at least about nine months, or at least about one year to four years following completion of the trastuzumab therapy.

As described herein, the extended neratinib regimen is used to decrease the rate of recurrence of HER-2/neu overexpressed/amplified breast cancer in patients. These rates may be measured at a time point six months, one year, three years, or five years following inception of treatment. The regimen involves providing neratinib to these patients following primary and neo/adjuvant therapy. In another embodiment, the extended neratinib is used to improve invasive disease free survival, DFS-DCIS, distant disease free survival, and/or time to distant recurrence in cancer patients.

This extended adjuvant therapy of the invention may involve only a single dose of neratinib post-completion of trastuzumab therapy. However, in another embodiment, the extended neratinib regimen is administered over a period of one month, two months, at least six months, at least one year, at least 18 months, or for longer periods as needed or desired. In another embodiment, the patients are treated with neratinib for about 8 months to about 5 years, about 12 months (one year) to about three years, or for longer or shorter periods as determined by a medical professional.

As used herein, the term "providing" with respect to providing a neratinib, means either directly administering the compound or composition, or administering a prodrug, derivative, or analog which will form an effective amount of the neratinib compound within the body.

As used herein and except where noted, the terms "individual", "subject" and "patient" are used interchangeably, and refer to any animal, including mammals, preferably mice, rats, other rodents, rabbits, dogs, cats, swine, cattle, sheep, horses, non-human primates, and humans. Desirably, the term "individual", "subject" or "patient" refers to a human. In most embodiments, the subjects or patients are in need of the therapeutic treatment. Accordingly, the term "subject" or "patient" as used herein means any mammalian patient or subject to which the claimed regimen can be administered.

As used herein, the term "effective amount" or "pharmaceutically effective amount" when administered to a subject to treat a neoplasm, is sufficient to inhibit, slow, reduce, or eliminate lesions or tumor growth in a subject, or to inhibit, slow, or reduce progression of disease and/or to increase progression-free survival rate of the subject.

Neratinib (or the selected HKI-272 compound) can be administered, e.g., orally, at a dose range of about 0.01 to 100 mg/kg. In one embodiment, neratinib is administered at a dose range of about 0.1 to about 90 mg/kg. In another embodiment, neratinib is administered at a dose range of about 1 to about 80 mg/kg. In a further embodiment, neratinib is administered at a dose range of about 10 to about 70 mg/kg. In yet another embodiment, neratinib is administered at a dose range of about 15 to about 60 mg/kg. In still a further embodiment, neratinib is administered at a dose range of about 20 to about 240 mg per day, at least about 40 mg, at least about 120 mg, or at least about 160 mg, on the days in the cycle on which it is administered. One of skill in the art could routinely perform empirical activity tests to determine the bioactivity of the compound in bioassays and thus determine what dosage to administer when the compound is delivered by another route.

In one embodiment, the oral dosage of neratinib is at least about 700 mg/week. In another embodiment, the oral dosage of neratinib is about 800 mg/week to at least to about 1700 mg/week. In another embodiment, the oral dosage of neratinib is about 840 mg/week to about 1680 mg/week. In another embodiment, the oral dosage of neratinib is about 900 mg/week to about 1600 mg/week. In a further embodiment, the oral dosage of neratinib is about 1000 mg/week to about 1500 mg/week. In yet another embodiment, the oral dosage of neratinib is about 1100 mg/week to about 1400 mg/week. In still a further embodiment, the oral dosage of neratinib is about 1200 mg/week to about 1300 mg/week. Precise dosages are determined by the administering physician based on experience with the individual subject to be treated. Other dosage regimens and variations are foreseeable, and are determined through physician guidance.

For neratinib, it is desired that the compound be in the form of a unit dose. Neratinib can be administered at a dose range of about 0.01 to 100 mg/kg or at a dose range of 0.1 to 10 mg/kg. In one embodiment, neratinib is administered orally from 1 to 6 times a day, more usually from 1 to 4 times a day. Suitable unit dose forms include tablets, capsules and powders in sachets or vials. Such unit dose forms may contain from 0.1 to 300 mg of neratinib, from 2 to 100 mg, at a dose of 120 mg to 300 mg daily, or 240 mg daily. Alternatively, neratinib may be administered through another suitable route, e.g., intravenous. In still another embodiment, neratinib is administered once a week. In certain situations, dosing with neratinib may be delayed or discontinued for a brief period (e.g., 1, 2 or three weeks) during the course of treatment. Such a delay or discontinuation may occur once, or more, during the course of treatment. The effective amount will be known to one of skill in the art; it will also be dependent upon the form of the compound. One of skill in the art could routinely perform empirical activity tests to determine the bioactivity of the compound in bioassays and thus determine what dosage to administer.

In one embodiment, suitable examples of pharmaceutical carriers used herein include, but are not limited to, excipients, diluents, fillers, disintegrants, lubricants and other agents that can function as a carrier. The term "pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous. Pharmaceutical compositions are prepared in accordance with acceptable pharmaceutical procedures, such as described in Remingtons Pharmaceutical Sciences, 17th edition, ed. Alfonoso R. Gennaro, Mack Publishing Company, Easton, Pa. (1985). Pharmaceutically acceptable carriers are those that are compatible with the other ingredients in the formulation and biologically acceptable. Suitable pharmaceutically-acceptable excipients or carriers for a tablet or caplet formulation include, e.g., inert excipients such as lactose, sodium carbonate, calcium phosphate or calcium carbonate, granulating and disintegrating agents such as corn starch or alginic acid; binding agents such as gelatin or starch; lubricating agents such as magnesium stearate, stearic acid or talc; preservative agents such as ethyl or propyl 4-hydroxybenzoate, and anti-oxidants, such as ascorbic acid. Tablet or caplet formulations may be uncoated or coated either to modify their disintegration and the subsequent absorption of the active ingredient within the gastrointestinal tract, or to improve their stability and/or appearance using conventional coating agents and procedures well known in the art.

In one embodiment, the invention provides an extended regimen for treatment of HER-2/neu overexpressed/amplified cancer comprising delivering a course of extended neratinib therapy to HER-2/neu overexpressed/amplified cancer patients. Such extended therapy involves beginning the neratinib therapy at the completion of surgical/or and adjuvant therapy. This extended therapy is used to provide improved invasive disease-free survival and/or improvements in overall survival, time to distant recurrence, and distant disease-free survival. As described herein, the extended neratinib regimen is initiated at least one, at least two, or at least three years following inception of initial therapy. In one embodiment, neratinib therapy is initiated at least about 2 weeks after and up to about four years following the completion of primary and standard neo/adjuvant therapy.

In one embodiment, selected concomitant therapies may be used in conjunction with the extended neratinib regimen. For example, patients may be further undergoing concomitant therapy with bisphosphonates for osteopenia or osteoporosis. In another example, patients may be further undergoing concomitant endocrine therapy. Optionally, such concomitant therapies may be non-adjuvant therapies, but rather are for treatment of other conditions or symptoms which the patient may have.

Pharmaceutical Packs/Kits

The invention includes a product or pharmaceutical pack containing a course of an anti-neoplastic treatment for one individual mammal comprising one or more container(s) having one, one to four, or more unit(s) of neratinib and, optionally, one, one to four, or more unit(s) of another active agent.

In another embodiment, pharmaceutical packs contain a course of anti-neoplastic treatment for one individual mammal comprising a container having a unit of a rapamycin in unit dosage form, a containing having a unit of neratinib and optionally, a container with another active agent.

In some embodiments, the compositions of the invention are in packs in a form ready for administration. In other embodiments, the compositions of the invention are in concentrated form in packs, optionally with the diluent required to make a final solution for administration. In still other embodiments, the product contains a compound useful in the invention in solid form and, optionally, a separate container with a suitable solvent or carrier for the compound useful in the invention.

In still other embodiments, the above packs/kits include other components, e.g., instructions for dilution, mixing and/or administration of the product, other containers, syringes, needles, etc. Other such pack/kit components will be readily apparent to one of skill in the art.

The following examples illustrate of the uses of the combinations of the invention. It will be readily understood that alterations or modifications, e.g., in the formulation of the components, the routes of delivery, and the dosing, can be made for reasons known to those of skill in the art.

EXAMPLES

Neratinib as a single agent has been studied in a phase 2 trial in subjects with metastatic erbB-2 positive breast cancer. Sixty-six subjects with prior trastuzumab based therapy were enrolled into Arm A; 70 subjects without any prior trastuzumab exposure were enrolled into Arm B. Objective response rate and median progression free survival were used as estimates of antitumor activity.

According to preliminary data based on independent radiology assessment, among subjects with prior trastuzumab treatment, the overall response rate (ORR) was 26% (95% confidence index (CI)) and median progression-free survival (PFS) was 23 weeks (95% CI). For subjects without prior exposure to trastuzumab, the ORR was 57% (95% CI) and median PFS was 40 weeks (95% CI). The antitumor activity in arm A provides the basis for the testing neratinib as a single agent in trastuzumab refractory subjects.

In Arm A, the median duration of trastuzumab exposure was 60 weeks. Twenty-eight (28%) of subjects received trastuzumab as adjuvant or neoadjuvant therapy. The majority (48%) of subjects received one trastuzumab based regimen in the metastatic setting and approximately 43% received a second or third trastuzumab based regimen for metastatic disease. Arm A subjects also had extensive prior cytotoxic treatment with 53% of subjects receiving 2-3 prior regimens and another 27% receiving >3 prior cytotoxic regimens. Taken together, these treatment characteristics described a heavily pretreated, and likely refractory, study population in Arm A. As such, an ORR of 26% in a refractory population suggests that neratinib is likely to be a highly active agent for erbB-2 positive breast cancer.

Main adverse event associated with neratinib is diarrhea, which has been generally well manageable with medication, treatment interruption, or dose modification. Other common adverse events are nausea, vomiting, fatigue, and anorexia.

Example 1

In a randomized, double-blind, placebo-controlled phase 3 trial, neratinib is compared against placebo following trastuzumab in women with early-stage HER-2/neu overexpressed/amplified breast cancer. Subjects must have completed a course of prior adjuvant trastuzumab. If less than 12 months of trastuzumab have been given, at least 8 prior doses must have been given and it must be specified that the subject is either not eligible or unable to receive further adjuvant therapy with trastuzumab. Following completion of a course of prior adjuvant therapy involving at least 8, and preferably 12 months of trastuzumab, subjects are eligible for treatment with the regimen described herein. The last dose of trastuzumab must have been given >2 weeks and <4 years from inception of randomization. Randomization will be stratified by the following factors: ER and/or PgR positive vs. ER and PgR negative; nodal status (0, 1-3, 4 or more); < or > 3 years from diagnosis; trastuzumab given sequentially vs. concurrently with chemotherapy.

Eligible subjects are randomly assigned in a 1:1 ratio to one of the following two arms: Neratinib 240 mg daily for 1 year or Placebo daily for 1 year. After discontinuing study treatment, subjects will continue to be followed for disease recurrence and survival until the planned number of invasive disease free survival (IDFS) events has been reached, and for survival thereafter until the end of the study. The primary efficacy endpoint of IDFS and time-to-event secondary endpoints will be analyzed using a stratified log-rank test. The hazard ratio and the corresponding 95% confidence interval will be derived from a stratified Cox proportional hazards regression model [D R Cox, 1972, "Regression Models and Life Tables (with Discussion)", Journal of the Royal Statistical Society, Series B 34:187-220]. The median times to event and the associated 95% confidence intervals will be estimated using the Kaplan-Meier method [Kaplan, E. L. and Meier, Paul. "Nonparametric estimation from incomplete observations." J. Am. Stat. Assoc. 53, 457-481 (1958)]. The primary efficacy analysis will be conducted on the intent to treat population, defined as all subjects randomized. Adverse events and serious adverse events will be summarized by treatment arm for the safety population, defined as all subjects dosed with neratinib or placebo. The incidence of grade 3 or higher diarrhea will also be summarized and differences across treatment arms will be tested using the Mantel-Haenszel test. [(Mantel N & Haenszel W. Statistical aspects of the analysis of data from retrospective studies of disease. *J. Nat. Cancer Inst.* 22:719-48, 1959].

All publications cited in this specification are incorporated herein by reference. While the invention has been described with reference to particular embodiments, it will be appreciated that modifications can be made without departing from the spirit of the invention. Such modifications are intended to fall within the scope of the appended claims.

The invention claimed is:

1. A regimen for treatment of early stage HER-2 positive breast cancer comprising delivering neratinib therapy to early stage HER-2 positive breast cancer patients at the completion of at least twelve cycles of trastuzumab adjuvant therapy; wherein the neratinib therapy is started about 2 weeks to about one year from the completion of surgical and standard adjuvant therapy.

2. The regimen according to claim 1, wherein the course of neratinib therapy is in the range of 8 months to 5 years.

3. The regimen according to claim 1, wherein the cancer patients are treated with neratinib for at least about 12 months.

4. The regimen according to claim 1, wherein neratinib is delivered orally.

5. The regimen according to claim 4, wherein neratinib is delivered in tablet form.

6. The regimen according to claim 1, wherein neratinib is administered daily.

7. The regimen according to claim 1, wherein neratinib is delivered at a dose of 120 mg to 300 mg daily.

8. The regimen according to claim 7, wherein neratinib is delivered at a dose of 240 mg.

9. A method for improving invasive disease-free survival (IDFS) or disease-free survival (DFS)-HER 2 positive ductal carcinoma in situ (DCIS) and/or improvements in overall survival, time to distant recurrence, and/distant disease-free survival in an early stage HER-2 positive breast cancer patient, said method comprising delivering neratinib to said patient following the completion of at least twelve cycles of trastuzumab adjuvant therapy; wherein the neratinib therapy is started about 2 weeks to about one year from the completion of surgical and standard adjuvant therapy.

10. The method according to claim 9, wherein the patient received standard adjuvant therapy consisting of trastuzumab and one or more chemotherapy.

11. The method according to claim 10, wherein the chemotherapy involved one or more of doxorubicin, cyclophosphamide, paclitaxel, docetaxel, carboplatin, lapatinib, pertuzumab, bevacizumab, trastuzumab-DM-1, and anthracycline based therapy.

12. A regimen for improving invasive disease free survival, disease-free survival-HER 2 positive ductal carcinoma in situ, overall survival, time to distant recurrence, and/or distant disease-free survival comprising treating early stage HER-2 positive breast cancer patients with neratinib for at least twelve months, wherein said treatment with neratinib following the completion of at least at least twelve cycles of adjuvant therapy with trastuzumab; and wherein the neratinib therapy is started about 2 weeks to about one year from the completion of surgical and standard adjuvant therapy.

13. The regimen according to claim 12, wherein the neratinib therapy commences about six months to about twelve months following the completion of trastuzumab therapy.

14. The regimen according to claim 12, wherein the patients are further undergoing concomitant therapy selected from one or more of bisphosphonates for osteopenia or osteoporosis and endocrine therapy.

15. The regimen according to claim 1, wherein the early stage HER-2 positive breast cancer patient is a hormone receptor positive patient.

16. The regimen according to claim 15, wherein the hormone receptor positive patient is an estrogen receptor or progesterone receptor positive patient.

17. The regimen according to claim 9, wherein the early stage HER-2 positive breast cancer patient is a hormone receptor positive patient.

18. The regimen according to claim 17, wherein the early stage HER-2 positive breast cancer patient is an estrogen receptor or progesterone receptor positive patient.

* * * * *